United States Patent
Chou et al.

(10) Patent No.: US 11,485,986 B2
(45) Date of Patent: Nov. 1, 2022

(54) CELLS AND METHODS FOR PRODUCTION OF LYSINE AND LYSINE-DERIVED PRODUCTS

(71) Applicants: CATHAY BIOTECH INC., Shanghai (CN); CIBT AMERICA INC., Newark, DE (US)

(72) Inventors: Howard Chou, Shanghai (CN); Ling Chen, Shanghai (CN); Yunfeng Lei, Shanghai (CN); Xiucai Liu, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 0 days.

(21) Appl. No.: 16/961,106

(22) PCT Filed: Jan. 9, 2018

(86) PCT No.: PCT/CN2018/071859
§ 371 (c)(1),
(2) Date: Jul. 9, 2020

(87) PCT Pub. No.: WO2019/136585
PCT Pub. Date: Jul. 18, 2019

(65) Prior Publication Data
US 2021/0054423 A1   Feb. 25, 2021

(51) Int. Cl.
| | |
|---|---|
| *C12P 13/08* | (2006.01) |
| *C12N 9/12* | (2006.01) |
| *C12N 9/88* | (2006.01) |
| *C12N 15/70* | (2006.01) |
| *C12P 13/00* | (2006.01) |

(52) U.S. Cl.
CPC ............ *C12P 13/08* (2013.01); *C12N 9/1217* (2013.01); *C12N 9/88* (2013.01); *C12N 15/70* (2013.01); *C12P 13/001* (2013.01); *C12Y 207/02004* (2013.01); *C12Y 401/0102* (2013.01); *C12Y 401/01018* (2013.01); *C12Y 403/03007* (2015.07)

(58) Field of Classification Search
None
See application file for complete search history.

(56) References Cited

U.S. PATENT DOCUMENTS

2009/0239269 A1 * 9/2009 Tajima .................. C12P 13/227
435/109

FOREIGN PATENT DOCUMENTS

| CN | 104388371 A | 3/2015 |
|---|---|---|
| EP | 2050816 A1 | 4/2009 |
| WO | 03046184 A1 | 6/2003 |
| WO | 2007119574 A2 | 10/2007 |
| WO | 2007119574 A3 | 10/2007 |
| WO | 2015196430 A1 | 12/2015 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession AF031251. Jan. 6, 2005 (Year: 2005).*
Accession AOG56193. Jan. 31, 2008. (Year: 2008).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
International Search Report and Written Opinion issued in corresponding Application No. PCT/CN2018/071859, dated Jan. 9, 2018, 8 pages.
Yakandawala, N. et al. "Metabolic engineering of *Escherichia coli* to enhance phenylalanine production" Appl. Microbial Biotechnol., vol. 78, No. 2, Dec. 15, 2007 (Dec. 15, 2007), pp. 283-291.
Lu, L.J. et al. "Improved production of L-tryptophan in *Escherichia coli* with csrB and tktA overexpression" Chin. J. Appl. Environ. Biol., vol. 21, No. 4, Aug. 25, 2015 (Aug. 25, 2015), pp. 647-651.
Extended European Search Report issued in corresponding European Application No. 18899629.2, dated Jul. 9, 2021, 8 pages.

* cited by examiner

*Primary Examiner* — Christian L Fronda
(74) *Attorney, Agent, or Firm* — Rothwell, Figg, Ernst & Manbeck, P.C.

(57) ABSTRACT

The invention provides microorganisms genetically modified to overexpress biofilm dispersal related polypeptides to enhance the production of lysine and lysine derivatives by the microorganism, method of generating such microorganism, and methods of producing lysine and lysine derivatives using the genetically modified microorganisms.

12 Claims, No Drawings

Specification includes a Sequence Listing.

CELLS AND METHODS FOR PRODUCTION OF LYSINE AND LYSINE-DERIVED PRODUCTS

CROSS REFERENCE TO RELATED APPLICATION(S)

This application is a 35 U.S.C. § 371 National Phase Entry Application from PCT/CN2018/071859, filed Jan. 9, 2018, designating the United States, the disclosure of which is incorporated herein in its entirety by reference.

BACKGROUND OF THE INVENTION

The ability for a molecule to move into and out of a cell can have a significant effect on the intracellular concentration of the molecule. For example, if the molecule is a nutrient, then slowing the movement of the molecule into the cell would inhibit growth (Herbert, D & HL Kornberg, *Biochem. J.* 156(2), 477-480, 1976). If the molecule is a toxin, then slowing the movement of the molecule out of the cell would inhibit growth. If the molecule is a substrate in a reaction, then slowing the movement of the molecule into the cell would slow down the rate of the reaction. If the molecule is an intermediate in a series of reactions, then slowing the movement of the molecule out of the cell and allowing it to accumulate inside the cell could lead to feedback inhibition (Kikuchi et al., *FEMS Microbiology Letters* 173:211-215, 1999; Ogawa-Miyata et al., *Biosci. Biotechnol. Biochem.* 65:1149-1154, 2001).

Previously, it was discovered that a phosphodiesterase protein that increases biofilm dispersal by reducing the intracellular concentration of bis-(3'-5')-cyclic diguanosine-monophosphate (c-di-GMP) affects the production of an amino acid, e.g., lysine, and its derived products, such as cadaverine (PCT/CN2016/095281). Although various genes have been shown to hydrolyze c-di-GMP and increase biofilm dispersal activity (e.g., bdcA or yahA from *E. coli*; rapA, fleN, rocR, or bifA from *P. aeruginosa*; vieA or mbaA from *V. cholerae*; and rmdAB from *S. coelicolor*), any effects of increasing biofilm dispersal activity by reducing intracellular c-di-GMP concentrations on the production of amino acids or their derivatives were unknown. PCT/CN2016/095281 demonstrates that a genetically modified microorganism in which a biofilm dispersal polypeptide is overexpressed relative to a counterpart microorganism of the same strain that does not comprise the genetic modification showed increased production of lysine or a lysine-derived compounds such as cadaverine.

Another set of genes that affects biofilm formation has also been identified. The carbon storage regulator (Csr) CsrA is a global regulatory protein that has been shown to repress biofilm formation and increase biofilm dispersal in *Escherichia coli* (Jackson et al., *J. Bacteriol.* 184: 290-301, 2002). It was shown that disruption of the csrA gene increased biofilm formation, and overexpression of csrA from a plasmid inhibited biofilm formation in *E. coli*. It has also been shown that CsrA is an mRNA binding protein that is part of the regulatory pathway affecting glycogen biosynthesis, catabolism, and gluconeogenesis (Romeo et al., *J. Bacteriol.* 175: 4744-4755, 1993). CsrA activity is inhibited by the binding of the sRNA CsrB, a non-coding RNA that consists of 18 imperfect repeats (5'-CAGGA(U,C,A)G-3') that form hairpin structures (Romeo et al., *Mol. Microbiol.* 29: 1321-1330, 1998). Therefore, part of the mechanism of inhibition is that 18 CsrA proteins bind to one CsrB molecule at the hairpin structures.

There are two additional proteins/sRNAs that are part of the Csr system. While CsrA regulates mRNA stability and plays a role at both the transcriptional and post-transcriptional levels, the CsrD protein acts as a signaling protein that leads to the positive transcriptional regulation of genes affected by the Csr regulatory system (Esquerre et al., *Scientific Reports* 6: 25057, 2016). The Csr system is additionally regulated by the sRNA CsrC that can also inhibit the activity of CsrA (Wellbacher et al., *Mol. Microbiol.* 48: 657-670, 2003). It has been shown that both CsrB and CsrC are also upregulated during nutrient poor conditions (Jonas et al., *FEMS Microbiol. Lett.* 297: 80-86).

The Csr system has previously been manipulated in order to increase the production of amino acids. For example, it was shown that increasing CsrA production by reducing the amount of CsrB can increase threonine production (WO 2003/046184). It was subsequently shown (EP 2050816 and US 2009/0258399) that deletion of csrB and csrC can increase amino acid production, specifically, that of arginine. EP 2055771 indicates that attenuation of csrB can increase amino acid production, and in U.S. Pat. No. 8,759,042, that deletion of csrC can increase arginine production. Interestingly, it has also been shown that increased expression of csrB can increase phenylalanine production (Yakandawala et al., *Appl. Microbiol. Biotechnol.* 78: 283-291, 2008) and tryptophan production (Lu et al., *Chin. J. Appl. Environ. Biol.* 21: 647-651, 2015). Thus, these publications demonstrate that increasing or decreasing CsrB or CsrC can either increase or decrease the production of an amino acid. Accordingly, one of skill would not be able to determine whether a specific amino acid different from those previously evaluated would be decreased or increased when CsrB or CsrC levels are manipulated in a cell.

BRIEF SUMMARY OF ASPECTS OF THE DISCLOSURE

The present disclosure is based, in part, on the surprising discovery that increasing the production of CsrA in *E. coli* does not increase lysine production; but instead, reduces lysine production; and that cells overexpressing either csrB or csrC showed increased lysine production.

Thus, in one aspect, provided herein is a genetically modified host cell comprising an exogenous nucleic acid encoding a CsrB sRNA or a CsrC sRNA, wherein the host cell overexpresses CsrB or CsrC relative to a counterpart host cell that has not been modified to express the exogenous nucleic acid; and has at least one additional genetic modification to increase production of lysine or a lysine derivative compared to a wildtype host cell. In some embodiments, the amino acid derivative is cadaverine. In some embodiments, the CsrB sRNA comprises a nucleotide sequence having at least 85% identity, or at least 90% identity, or at least 95% identity, to SEQ ID NO:16. In some embodiments, CsrC sRNA comprises a nucleotide sequence having at least 85% identity, or at least 90% identity, or at least 95% identity, to SEQ ID NO:17. In particular embodiments, the CsrB sRNA comprises the nucleic acid sequence of SEQ ID NO:16. In other embodiments, the CsrC sRNA comprises the nucleic acid sequence of SEQ ID NO:17. In some embodiments, the CsrB or CsrC sRNA is heterologous to the host cell. In some embodiments, the exogenous nucleic acid encoding the CsrB or CsrC sRNA is encoded by an expression vector introduced into the cell, wherein the expression vector comprises the exogenous nucleic acid operably linked to a promoter. In other embodiments, the exogenous nucleic acid is integrated into the host chromosome. In some embodiments, the host cell overexpresses a lysine decarboxylase. In further embodiments, the host cell overexpresses one or more lysine biosynthesis polypeptides, such as an aspartate kinase, a dihydrodipicolinate synthase, a diaminopimelate decarboxylase, an aspartate semialdehyde dehydrogenase, a dihydropicolinate reductase, or an aspartate transaminase. In particular embodiments, the aspartate kinase, dihydrodipicolinate synthase, diaminopimelate decarboxylase, aspartate semialdehyde dehydrogenase, adihydropicolinate reductase, or aspartate transaminase is a LysC, DapA, LysA, Asd, DapB, or AspC polypeptide. In certain embodiments, the host cell overexpresses a CadA, LysC, DapA, LysA, Asd, DapB, and AspC polypeptide. In some embodiments, the host cell is of the genus *Escherichia*, *Hafnia*, or *Corynebacterium*. In particular embodiments, the host cell is *Escherichia coli*, *Hafnia alvei*, or *Corynebacterium glutamicum*.

In an additional aspect, provided herein is a method of producing lysine or a lysine derivative, e.g., cadaverine, the method comprising culturing a host cell as described herein, e.g., in the preceding paragraph under conditions in which the CsrB sRNA or CsrC sRNA is overexpressed.

In a further aspect, provided herein is a method of engineering a host cell to increase production of lysine or a lysine derivative, the method comprising introducing an exogenous nucleic acid encoding a CsrB sRNA or CsrC sRNA into the host cell, wherein the host cell has at least one additional genetic modification to increase production of lysine or a lysine derivative compared to a wildtype host cell; culturing the host cell under conditions in which the CsrB or CsrC sRNA is expressed, and selecting a host cell that exhibits increased production of lysine or a lysine derivative relative to a counterpart control host cell that has not been modified to express the exogenous nucleic acid. In some embodiments, the amino acid derivative is cadaverine. In some embodiments, the CsrB sRNA comprises a nucleotide sequence having at least 85% identity, or at least 90% identity, or at least 95% identity, to SEQ ID NO:16. In some embodiments, the CsrC sRNA comprises a nucleotide sequence having at least 85% identity, or at least 90% identity, or at least 95% identity, to SEQ ID NO:17. In further embodiments, the CsrB sRNA comprises the nucleic acid sequence of SEQ ID NO:16. In other embodiments, the CsrC sRNA comprises the nucleic acid sequence of SEQ ID NO:17. In some embodiments, the CsrB sRNA or CsrC sRNA is heterologous to the host cell. In some embodiments, the exogenous nucleic acid encoding the CsrB or CsrC sRNA is encoded by an expression vector introduced into the cell, wherein the expression vector comprises the exogenous nucleic acid operably linked to a promoter. In other embodiments, the exogenous nucleic acid is integrated into the host chromosome. In some embodiments, the host cell overexpresses a lysine decarboxylase. In some embodiments, the host cell overexpresses one or more lysine biosynthesis polypeptides, such as an aspartate kinase, a dihydrodipicolinate synthase, a diaminopimelate decarboxylase, an aspartate semialdehyde dehydrogenase, a dihydropicolinate reductase, or an aspartate transaminase. In some embodiments, the aspartate kinase, dihydrodipicolinate synthase, diaminopimelate decarboxylase, aspartate semialdehyde dehydrogenase, adihydropicolinate reductase, or aspartate transaminase is a LysC, DapA, LysA, Asd, DapB, or AspC polypeptide. In some embodiments, the host cell overexpresses a CadA, LysC, DapA, LysA, Asd, DapB, and AspC polypeptide. In some embodiments, the host cell is of the genus *Escherichia*, *Hafnia*, or *Corynebacterium*. In certain embodiments, the host cell is *Escherichia coli*, *Hafnia alvei*, or *Corynebacterium glutamicum*.

DETAILED DESCRIPTION OF THE INVENTION

Terminology

As used herein, "CsrB" refers to a small regulatory RNA (sRNA) that comprises imperfect repeats that form hairpin structures and binds CsrA. "CsrB" includes *E. coli* CsrB and homologs of CsrB from other bacteria, such as member of the Enterobacteriaceae family. *E. coli* CsrB is about 360 nucleotides in length and contains 18 imperfect repeats 5'-CAGGA(U,C,A)G-3') (Romeo et al., *Mol. Microbiol.* 29: 1321-1330, 1998). CsrA binds to CsrB at the hairpin structures such that one molecule of CsrA binds to each hairpin structure. Thus, CsrB sequesters CsrA and reduces CsrA activity. CsrA/CsrB sequences have been reported in other Enterobacteriaceae, such as *Salmonella*, *Shigella*, and *Yersinia*. In *Salmonella*, CsrB has been shown to have 16 predicted stem-loops, each carrying the consensus sequence GWGGRHG (Altier, et al. *Mol. Microbiol.* 35:635-646, 2000), where "W" is A or U; R is A or G; and H is A, C, or U. An illustrative *E. coli* CsrB DNA sequence is provided in SEQ ID NO:16. Additional CsrB sequences include those encoded by chromosomal region CP015574.1 of a *Salmonella enterica* subsp; chromosomal region CP024470.1 of *Shigella flexneri*; chromosomal region CP023645.1 of *Shigella sonnei*; and chromosomal region LT556085.1 of *Citrobacter* sp.

As used herein, "CsrC" refers to an sRNA that comprises imperfect repeats similar to those contained in CsrB that form hairpin structures and binds CsrA, thus sequestering CsrA. The term includes *E. coli* CsrC and homologs of CsrC from other bacteria, such as member of the Enterobacteriaceae family. *E. coli* CsrC is about 245 nucleotides in length and contains 9 such repeats (Weilbacher et al., *Mol. Microbiol.* 48:657-670, 2003). In *Salmonella*, CsrC has been shown to have 8 predicted stem-loop structures (Fortune et al., *Infect. And Immun.* 74:1331-1339, 2006). An illustrative *E. coli* CsrC DNA sequence is provided in SEQ ID NO:17. Additional CsrC sequences include those encoded by chromosomal region CP023645.1 of *Shigella sonnei*; chromosomal region CP024470.1 of *Shigella flexneri*; CP023504.1 of *Citrobacter werkmanii*; and chromosomal region CP018661.1 of *Salmonella enterica* subsp.

The terms "increased expression" and "overexpression" of a CsrB or CsrC sRNA are used interchangeably herein to refer to an increase in the amount of CsrB or CsrC sRNA in a genetically modified cell, e.g., a cell into which an expression construct encoding a CsrB or CsrC sRNA has been introduced, compared to the amount of CsrB or CsrC sRNA in a counterpart cell that does not have the genetic modification, i.e., a cell of the same strain without the modification. An increased level of expression for purposes of this application is typically at least 5%, or at least 10%, 20%, 30%, 40%, 50%, 60%, 70%, 80%, 90%, 100%, or greater, compared to the counterpart unmodified cell. The unmodified cell need not express the CsrB or CsrC sRNA. Thus, the term "overexpression" also includes embodiments in which a CsrB or CsrC sRNA is expressed in a host cell that does not natively express the CsrB or CsrC sRNA. Increased expression of a CsrB or CsrC sRNA can be assessed by any number of assays, including, but not limited to, measuring the level of RNA and/or the level of CsrB or CsrC sRNA activity, e.g., by measuring CsrA binding activity directly or by assessing an activity modulated by CsrB or CsrC sRNA.

The term "enhanced" in the context of the production of lysine, or a lysine derivative such as cadaverine, as used herein refers to an increase in the production of amino acid, e.g., lysine, or the derivative, by a genetically modified host cell in comparison to a control counterpart cell, such as a cell of the wildtype strain or a cell of the same strain that does not have the genetic modification to increase production of lysine or the lysine derivative. Production of the amino acid or its derivative is typically enhanced by at least 5%, or at least 0%, 20%, 30%, 40%, 50%, 60%, 70%, 80%, 90%, 100%, or greater compared to the control cell.

The terms "numbered with reference to", or "corresponding to," or "determined with reference to" when used in the context of the numbering of a given amino acid or polynucleotide sequence, refers to the numbering of the residues of a specified reference sequence when the given amino acid or polynucleotide sequence is compared to the reference sequence. For example, a nucleotide in a CsrB or CsrC sRNA sequence variant "corresponds to" a nucleotide position in SEQ ID NO:16 when the residue aligns with the nucleotide in a comparison of SEQ ID NO:16 and variant in a maximal alignment.

The terms "polynucleotide" and "nucleic acid" as used herein in the context of expression vectors and a sequence encoding a CsrB or CsrC sRNA are used interchangeably and refer to a single or double-stranded polymer of deoxyribonucleotide or ribonucleotide bases read from the 5' to the 3' end. A nucleic acid as used in the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Nucleic acids or polynucleotides may also include modified nucleotides that permit correct readthrough by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence, e.g., that encodes a polypeptide, also implicitly encompasses variants degenerate codon substitutions and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. Nucleic acid sequences are presented in the 5' to 3' direction unless otherwise specified.

The term "substantially identical" used in the context of two nucleic acids or polypeptides, refers to a sequence that has at least 60%, 65%, or 70% sequence identity with a reference sequence. Percent identity can be any integer from 60% to 100%. Some embodiments include at least: 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard default parameters, as described below.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

An algorithm that may be used to determine whether a CsrB or CsrC sRNA has sequence identity to SEQ ID NO:16 or 17, or another polynucleotide reference sequence, is the BLAST algorithm, which is described in Altschul et al., 1990, J. Mol. Biol. 215:403-410, which is incorporated herein by reference. Software for performing BLAST and BLAST2 analyses is publicly available through the National Center for Biotechnology Information (on the worldwide web at ncbi.nlm.nih.gov/).

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a repressor binding sequence and the like. These cis-acting sequences typically interact with proteins or other biomolecules to carry out (turn on/off, regulate, modulate, etc.) gene transcription. Most often the core promoter sequences lie within 1-2 kb of the translation start site, more often within 1 kbp and often within 500 bp or 200 bp or fewer, of the translation start site. By convention, promoter sequences are usually provided as the sequence on the coding strand of the gene it controls. In the context of this application, a promoter is typically referred to by the name of the gene for which it naturally regulates expression. A promoter used in an expression construct of the invention is thus referred to by the name of the gene. Reference to a promoter by name includes a wild type, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription under most conditions in a cell, e.g., in the absence of an inducing molecule. An "inducible promoter" initiates transcription in the presence of an inducer molecule.

As used herein, a polynucleotide is "heterologous" to an organism or a second polynucleotide sequence if it originates from a foreign species, or, if from the same species, is modified from its original form. For example, when a polynucleotide encoding a CsrB or CsrC sRNA sequence is said to be operably linked to a heterologous promoter, it means that the polynucleotide coding sequence encoding the CsrB or CsrC is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different species). Similarly, a CsrB or CsrC sRNA, or a polynucleotide encoding the a CsrB or CsrC sRNA is "heterologous" to a host cell if the native wildtype host cell does not produce the a CsrB or CsrC sRNA; and a CsrB sRNA or CsrC sRNA variant is "heterologous" to a host cell if the nucleotide sequence differs from a CsrB or CsrC polynucleotide sequence that is native to the host cell.

The term "exogenous" as used herein refers generally to a polynucleotide sequence or polypeptide that is introduced into a host cell by molecular biological techniques to produce a recombinant cell. Examples of "exogenous" polynucleotides include vectors, plasmids, and/or man-made nucleic acid constructs encoding a desired protein. An "exogenous" polypeptide or polynucleotide expressed in the host cell may occur naturally in the wildtype host cell or may be heterologous to the host cell. The term also encompasses progeny of the original host cell that has been engineered to express the exogenous polynucleotide or polypeptide sequence, i.e., a host cell that expresses an "exogenous" polynucleotide may be the original genetically modified host cell or a progeny cell that comprises the genetic modification.

The term "endogenous" refers to naturally-occurring polynucleotide sequences or polypeptides that may be found in a given wild-type cell or organism. In this regard, it is also noted that even though an organism may comprise an endogenous copy of a given polynucleotide sequence or gene, the introduction of an expression construct or vector encoding that sequence, such as to over-express or otherwise regulate the expression of the encoded protein, represents an "exogenous" copy of that gene or polynucleotide sequence. Any of the pathways, genes, RNAs, or enzymes described herein may utilize or rely on an "endogenous" sequence, which may be provided as one or more "exogenous" polynucleotide sequences, or both.

"Recombinant nucleic acid" or "recombinant polynucleotide" as used herein refers to a genetically engineered polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence will have two or more sequences from unrelated genes arranged to make a new functional nucleic acid. A "recombinant" nucleic acid refers to the original polynucleotide that is manipulated as well as copies of the polynucleotide.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a polypeptide for use in the invention operably linked to a promoter, e.g., its native promoter, where the expression cassette is introduced into a heterologous microorganism. In some embodiments, an expression cassette comprises a polynucleotide sequence encoding a polypeptide of the invention where the polynucleotide that is targeted to a position in the genome of a microorganism such that expression of the polynucleotide sequence is driven by a promoter that is present in the microorganism.

The term "host cell" as used in the context of this invention refers to a microorganism and includes an individual cell or cell culture that can be or has been a recipient of any recombinant vector(s) or isolated polynucleotide(s) of the invention. Host cells include progeny of a single host cell, and the progeny may not necessarily be completely identical (in morphology or in total DNA complement) to the original parent cell due to natural, accidental, or deliberate mutation and/or change. A host cell includes cells into which a recombinant vector or a polynucleotide of the invention has been introduced, including by transformation, transfection, and the like.

The term "isolated" refers to a material that is substantially or essentially free from components that normally accompany it in its native state. For example, an "isolated polynucleotide," as used herein, may refer to a polynucleotide that has been isolated from the sequences that flank it in its naturally-occurring or genomic state, e.g., a DNA fragment that has been removed from the sequences that are normally adjacent to the fragment, such as by cloning into a vector. A polynucleotide is considered to be isolated if, for example, it is cloned into a vector that is not a part of the natural environment, or if it is artificially introduced in the genome of a cell in a manner that differs from its naturally-occurring state Aspects of the Disclosure The present disclosure is based, in part, on the discovery that increased expression of a CsrB or CsrC sRNA in a microorganism, such as a gram-negative bacterium, enhances lysine production and/or production of a derivative of lysine, such as cadaverine.

A host cell that is engineered in accordance with the invention to overexpress a CsrB or CsrC sRNA also overexpresses at least one enzyme involved in the synthesis of an amino or amino acid derivative, such as a lysine decarboxylase polypeptide; and/or an additional polypeptide that is involved in amino acid biosynthesis. Lysine decarboxylase and lysine biosynthesis polypeptides and nucleic acid sequences are available in the art.

The invention employs various routine recombinant nucleic acid techniques. Generally, the nomenclature and the laboratory procedures in recombinant DNA technology described below are commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009-2017).

Polynucleotides Encoding CsrB or CsrC sRNAs

Various polynucleotides have been shown to encode CsrB and CsrC sRNAs that bind to CsrA and reduce CsrA function. Polynucleotides that encode CsrB and CsrC sRNAs suitable for overexpressing in a host cell to increase production of lysine, or a derivative of lysine, include *E. coli* CsrB and CsrC polynucleotide sequences illustrated by SEQ ID NO:16 and SEQ ID NO:17, respectively.

In some embodiments, a host cell is genetically modified to overexpress a CsrB polynucleotide having at least 60%, or at least 70%, 75%, 80%, 85%, or at least 90% identity to SEQ ID NO:16. Unless indicated otherwise, "SEQ ID NO:16" refers to the DNA sequence shown in the listing of illustrative sequences and to its RNA counterpart in which uracil bases replace the thymine bases. Thus, when a CsrB RNA sequence is compared to SEQ ID NO:16 for determining percent identity, it is understood that SEQ ID NO:16 would contain "U" instead of "T". CsrB polynucleotide variants of SEQ ID NO:16 retain the ability to bind CsrA. In some embodiments, a CsrB polynucleotide has at least 85% identity; or at least 90%, or at least 95% identity to SEQ ID NO:16. In some embodiments, the polynucleotide comprises the sequence of SEQ ID NO:16. Additional illustrative CsrB sequences include those set forth in SEQ ID NOS:18, 19, 20, 21, and 22 from *Shigella, Triticum, Citrobacter*, and *Salmonella*, which have 99% sequence identity (*Shigella* and *Triticum*), 90% sequence identity (*Citrobacter*) and 87% sequence identity (*Salmonella*) to SEQ ID NO:16.

In some embodiments, a host cell is genetically modified to overexpress a CsrC polynucleotide having at least 60%, or at least 70%, 75%, 80%, 85%, or at least 90% identity to SEQ ID NO:17. Unless indicated otherwise, "SEQ ID NO:17" refers to the DNA sequence shown in the listing of illustrative sequences and to its RNA counterpart in which uracil bases replace the thymine bases. Thus, when a CsrC RNA sequence is compared to SEQ ID NO:17 for determining percent identity, it is understood that SEQ ID NO:17 would contain "U" instead of "T". CsrC polynucleotide variants of SEQ ID NO:17 retain the ability to bind CsrA. In some embodiments, a CsrC polynucleotide has at least 85% identity; or at least 90%, or at least 95% identity to SEQ ID NO:17. In some embodiments, the polynucleotide comprises the sequence of SEQ ID NO:17. Additional illustrative CsrC sequences include SEQ ID NOS:23, 24, 25, and 26 from *Shigella sonnei, Shigella flexneri, Citrobacter werkmanii*, and *Salmonella enterica*, which have 100%, 99%, 89%, and 88% sequence identity to SEQ ID NO:17, respectively.

In some embodiments, the CsrB or CsrC sRNA comprises at least 8, or at least 9, 10, 11, 12, 13, 14, 15, 16, 17, or 18; and typically fewer than 20 hairpins that bind CsrA. In some embodiments, the hairpin structure comprises the sequence GWGGRHG, in which "W" is A or U; R is A or G; and H is A, C, or U. In some embodiments, the hairpin structure comprises the sequence CAGGA(U,C,A)G.

In some embodiments, a host cell is genetically modified to over express a CsrB or CsrC sRNA from *Salmonella, Citrobacter*, or *Shigella*.

Activity of a wild-type or variant CsrB or CsrC sRNA can be assessed using any number of assays, including assays that evaluate the production of lysine or a lysine-derived compound. In some embodiments, lysine production or cadaverine production is measured. Illustrative assays are provided in the examples section. In some embodiments, cadaverine production is measured in *E. coli* modified to co-express LysC, DapA, LysA, Asd, DapB, AspC, and CadA and the CsrB or CsrC sRNA. The following is an illustrative assay that is used to assess production of lysine and/or cadaverine. *E. coli* are modified to express LysC, DapA, LysA, Asd, DapB, AspC, and CadA and the CsrB or CsrC sRNA. The genes may be individually introduced into *E. coli*, or introduced in one or more operons. For examples, LysC, DapA, LysA, Asd, DapB, and AspC may be encoded by a synthetic operon present in one plasmid and CadA and a candidate variant may be encoded by a separate plasmid. Each plasmid has a unique antibiotic-resistance selectable marker. Antibiotic-resistant colonies are selected and cultured. For example, cultures are grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, and appropriate antibiotics for selection. The following day, each culture is inoculated into 50 mL of fresh medium with 30 g/L of glucose, 0.7% $Ca(HCO_3)_2$, antibiotic(s), and grown for 72 hours at 37° C., at which point the concentration of lysine is determined. Lysine or cadaverine can be quantified using NMR.

Yield can be calculated by dividing the molar amount of lysine or cadaverine produced by the molar amount of glucose added. A CsrB or CsrC sRNA useful in this invention increases the yield of lysine or a cadaverine. Alternatively, colonies are evaluated for increased production of another lysine derivative.

In some embodiments, a CsrB or CsrC sRNA increases lysine or cadaverine production by at least 10%, at least 20%, at least 30%, at least 40%, at least 50% or greater, when expressed in a host cell compared to a counterpart host cell of the same strain that comprises the same genetic modifications other than the modification to overexpress the CsrB or CsrC sRNA. In some embodiments, CsrB or CsrC sRNA increases lysine or cadaverine production by at least 10%, at least 20%, at least 30%, at least 40%, at least 50% or greater, when expressed in a host cell that is modified to overexpress a lysine decarboxylase, an aspartate kinase, a dihydrodipicolinate synthase, a diaminopimelate decarboxylase, an aspartate semialdehyde dehydrogenase, a dihydropicolinate reductase, and an aspartate transaminase; compared to a counterpart host cell of the same strain that comprises the modification to overexpress the lysine decarboxylase, the aspartate kinase, the dihydrodipicolinate synthase, the diaminopimelate decarboxylase, the aspartate semialdehyde dehydrogenase, the dihydropicolinate reductase, and the aspartate transaminase, but does not overexpress the CsrB or CsrC sRNA.

In some embodiments, activity of a CsrB or CsrC sRNA can be assessed by determining the ability of the RNA to bind CsrA, e.g., in a quantitative mobility shift assay.

Isolation or generation of CsrB or CsrC sequences to incorporate into expression cassettes for overexpression in a host cell can be accomplished by a number of techniques. Such techniques will be discussed in the context of CsrB or CsrC polynucleotide sequences. However, one of skill understands that the same techniques can be used to isolate and express other desired genes. In some embodiments, oligonucleotide probes based on the sequences disclosed here can be used to identify the desired polynucleotide in a cDNA or genomic DNA library from a desired bacterial species. Probes may be used to hybridize with genomic DNA to isolate homologous genes in the same or different species.

In typical embodiments, the nucleic acids of interest are amplified from nucleic acid samples using routine amplification techniques. For instance, PCR may be used to amplify the sequences directly from genomic DNA. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for generating CsrB and CsrC polynucleotides in bacteria can be determined from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). Illustrative primer sequences are shown in the Table of Primers in the Examples section.

Nucleic acid sequences encoding a CsrB or CsrC sRNA that confers increased production of lysine, or a lysine-derived product, e.g., cadaverine, to a host cell, may additionally be codon-optimized for expression in a desired host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See e.g., Henaut and Danchin in "*Escherichia coli* and *Salmonella*," Neidhardt, et al. Eds., ASM Pres, Washington D.C. (1996), pp. 2047-2066; Nucleic Acids Res. 20:2111-2118; Nakamura et al., 2000, Nucl. Acids Res. 28:292).

Preparation of Recombinant Vectors

Recombinant vectors for expression of a CsrB or CsrC sRNA can be prepared using methods well known in the art. For example, a DNA sequence encoding a CsrB or CsrC sRNA (described in further detail below), can be combined with transcriptional and other regulatory sequences which will direct the transcription of the sequence from the gene in the intended cells, e.g., bacterial cells such as *E. coli*. In some embodiments, an expression vector that comprises an expression cassette that comprises the polynucleotide encoding a CsrB or CsrC sRNA further comprises a promoter operably linked to the CsrB or CsrC polynucleotide. In other embodiments, a promoter and/or other regulatory elements that direct transcription of the CsrB or CsrC polynucleotide are endogenous to the host cell and an expression cassette comprising the CsrB or CsrC polynucleotide is introduced, e.g., by homologous recombination, such that the exogenous CsrB or CsrC polynucleotide is operably linked to an endogenous promoter and expression is driven by the endogenous promoter.

As noted above, expression of a CsrB or CsrC polynucleotide can be controlled by a number of regulatory sequences including promoters, which may be either constitutive or inducible; and, optionally, repressor sequences, if desired. Examples of suitable promoters, especially in a bacterial host cell, are the promoters obtained from the *E. coli* lac operon and other promoters derived from genes involved in the metabolism of other sugars, e.g., galactose and maltose. Additional examples include promoters such as the trp promoter, bla promoter bacteriophage lambda PL, and T5. In addition, synthetic promoters, such as the tac promoter (U.S. Pat. No. 4,551,433), can be used. Further examples of promoters include *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes. Suitable promoters are also described in Ausubel and Sambrook & Russell, both supra. Additional promoters include promoters described by Jensen & Hammer, *Appl. Environ. Microbiol.* 64:82, 1998; Shimada, et al., *J. Bacteriol.* 186:7112, 2004; and Miksch et al., *Appl. Microbiol. Biotechnol.* 69:312, 2005.

In some embodiments, a promoter that influences expression of a native CsrB or CsrC polynucleotide may be modified to increase expression. For example, an endogenous CsrB or CsrC promoter may be replaced by a promoter that provides for increased expression compared to the native promoter.

An expression vector may also comprise additional sequences that influence expression of a polynucleotide encoding the CsrB or CsrC sRNA. Such sequences include enhancer sequences, a ribosome binding site, or other sequences such as transcription termination sequences, and the like.

A vector expressing a nucleic acid encoding a CsrB or CsrC sRNA may be an autonomously replicating vector, i.e., a vector which exists as an extrachromosomal entity, the replication of which is independent of chromosomal replication, e.g., a plasmid, an extrachromosomal element, a mini-chromosome, or an artificial chromosome. The vector may contain any means for assuring self-replication. Alternatively, the vector may be one which, when introduced into the host, is integrated into the genome and replicated together with the chromosome(s) into which it has been integrated. Thus, an expression vector may additionally contain an element(s) that permits integration of the vector into the host's genome.

An expression vector of the invention preferably contains one or more selectable markers which permit easy selection of transformed hosts. For example, an expression vector may comprise a gene that confers antibiotic resistance (e.g., ampicillin, kanamycin, chloramphenicol or tetracycline resistance) to the recombinant host organism, e.g., a bacterial cell such as E. coli.

Although any suitable expression vector may be used to incorporate the desired sequences, readily available bacterial expression vectors include, without limitation: plasmids such as pSClOl, pBR322, pBBRlMCS-3, pUR, pET, pEX, pMRlOO, pCR4, pBAD24, p15a, pACYC, pUC, e.g., pUC18 or pUC19, or plasmids derived from these plasmids; and bacteriophages, such as Ml 3 phage and λ phage. One of ordinary skill in the art, however, can readily determine through routine experimentation whether any particular expression vector is suited for any given host cell. For example, the expression vector can be introduced into the host cell, which is then monitored for viability and expression of the sequences contained in the vector.

Expression vectors of the invention may be introduced into the host cell using any number of well-known methods, including calcium chloride-based methods, electroporation, or any other method known in the art.

Host Cells

The present invention provides for a genetically modified host cell that is engineered to overexpress a CsrB or CsrC sRNA. Such a host cell may comprise a nucleic acid encoding a heterologous CsrB or CsrC sRNA, including any non-naturally occurring CsrB or CsrC sRNA variant; or may be genetically modified to overexpress a native CsrB or CsrC sRNA relative to a wildtype host cell.

A genetically modified host strain of the present invention typically comprises at least one additional genetic modification to enhance production of lysine or a lysine derivative relative to a control strain that does not have the one additional genetic modification, e.g., a wildtype strain or a cell of the same strain without the one additional genetic modification. An "additional genetic modification to enhance production of lysine or lysine derivative" can be any genetic modification. In some embodiments, the genetic modification is the introduction of a polynucleotide that expresses an enzyme involved in the synthesis of lysine or a derivative such as cadaverine. In some embodiments, the host cell comprises multiple modifications to increase production, relative to a wildtype host cell, of lysine or a lysine derivative, e.g., cadaverine.

In some aspects, genetic modification of a host cell to overexpress CsrB or CsrC sRNA is performed in conjunction with modifying the host cell to overexpress a lysine decarboxylase polypeptide and/or one or more lysine biosynthesis polypeptides.

A lysine decarboxylase refers to an enzyme that converts L-lysine into cadaverine. The enzyme is classified as E.C. 4.1.1.18. Lysine decarboxylase polypeptides are well characterized enzymes, the structures of which are well known in the art (see, e.g., Kanjee, et al., EMBO J. 30: 931-944, 2011; and a review by Lemmonier & Lane, Microbiology 144; 751-760, 1998; and references described therein). The EC number for lysine decarboxylase is 4.1.1.18. Illustrative lysine decarboxylase sequences are CadA homologs from Klebsiella sp., WP 012968785.1; Enterobacter aerogenes, YP 004592843.1; Salmonella enterica, WP 020936842.1; Serratia sp., WP 033635725.1; and Raoultella ornithinolytica, YP 007874766.1; and LdcC homologs from Shigella sp., WP 001020968.1; Citrobacter sp., WP 016151770.1; and Salmonella enterica, WP 001021062.1. As used herein, a lysine decarboxylase includes variants of native lysine decarboxylase enzymes that have lysine decarboxylase enzymatic activity. Additional lysine decarboxylase enzymes are described in PCT/CN2014/080873 and PCT/CN2015/072978.

In some embodiments, a host cell may be genetically modified to express one or more polypeptides that affect lysine biosynthesis. Examples of lysine biosynthesis polypeptides include the E. coli genes SucA, Ppc, AspC, LysC, Asd, DapA, DapB, DapD, ArgD, DapE, DapF, LysA, Ddh, PntAB, CyoABE, GadAB, YbjE, GdhA, GltA, SucC, GadC, AcnB, PflB, ThrA, AceA, AceE, GltB, AceF, SdhA, MurE, SpeE, SpeG, PuuA, PuuP, and YgjG, or the corresponding genes from other organisms. Such genes are known in the art (see, e.g., Shah et al., J. Med. Sci. 2:152-157, 2002; Anastassiadia, S. Recent Patents on Biotechnol. 1: 11-24, 2007). See, also, Kind, et al., Appl. Microbiol. Biotechnol. 91: 1287-1296, 2011 for a review of genes involved in cadaverine production. Illustrative genes encoding lysine biosynthesis polypeptides are provided below.

| Protein | Gene | EC Number | GenBank Accession No. |
|---|---|---|---|
| α-ketogultarate dehydrogenase (SucA) | sucA | 1.2.4.2 | YP_489005.1 |
| Phosphoenolpyruvate carboxylase (PPC) | ppc | 4.1.1.31 | AAC76938.1 |
| aspartate transaminase (AspC) | aspC | 2.6.1.1 | AAC74014.1 |
| aspartate kinase (LysC) | lysC | 2.7.2.4 | NP_418448.1 |
| aspartate semialdehyde dehydrogenase (Asd) | asd | 1.2.1.11 | AAC76458.1 |
| dihydrodipicolinate synthase (DapA) | dapA | 4.3.3.7 | NP_416973.1 |
| dihydropicolinate reductase (DapB) | dapB | 1.17.1.8 | AAC73142.1 |
| tetrahydrodipicoinate succinylase (DapD) | dapD | 2.3.1.117 | AAC73277.1 |
| N-succinyldiaminopimelate aminotransferase (ArgD) | argD | 2.6.1.11 | AAC76384.1 |
| N-succinyl-L-diaminopimelate deacylase (DapE) | dapE | 3.5.1.18 | AAC75525.1 |
| diaminopimelate epimerase (DapF) | dapF | 5.1.1.7 | AAC76812.2 |
| diaminopimelate decarboxylase (LysA) | lysA | 4.1.1.20 | AAC75877.1 |
| meso-diaminopimelate dehydrogenase (Ddh) | ddh | NA | P04964.1 |
| pyridine nucleotide transhydrogenase (PntAB) | pntAB | NA | AAC74675.1, AAC74674.1 |
| cytochrome O oxidase (CyoABE) | cyoABE | 1.10.3.10 | AAC73535.1, AAC73534.1, AAC73531.1 |
| glutamate decarboxylase (GadAB) | gadAB | 4.1.1.15 | AAC76542.1, AAC74566.1 |
| L-amino acid efflux transporter (YbjE) | ybjE | NA | AAC73961.2 |
| glutamate dehydrogenase (GdhA) | gdhA | 1.4.1.4 | AAC74831.1 |
| citrate synthase (GltA) | gltA | 2.3.3.1/ 2.3.3.16 | AAC73814.1 |

| Protein | Gene | EC Number | GenBank Accession No. |
| --- | --- | --- | --- |
| succinyl-coA synthase (SucC) | sucC | 6.2.1.5 | AAC73822.1 |
| glutamate-GABA antiporter (GadC) | gadC | NA | AAC74565.1 |
| aconitase B (AcnB) | acnB | 4.2.1.99 | AAC73229.1 |
| pyruvate-formate lyase (PflB) | pflB | NA | AAC73989.1 |
| aspartate kinase/homoserine dehydrogenase (ThrA) | thrA | 2.7.2.4 | AAC73113.1 |
| isocitrate lyase (AceA) | aceA | 4.1.3.1 | AAC76985.1 |
| malate synthase (AceB) | aceB | 2.3.3.9 | AAC76984.1 |
| glutmate synthase (GltB) | gltB | 1.4.1.13 | AAC76244.2 |
| pyruvate dehydrogenase (AceE) | aceE | 1.2.4.1 | AAC73225.1 |
| succinate dehydrogenase (SdhA) | sdhA | 1.3.5.1 | AAC73817.1 |
| UDP-N-acetylmuramoyl-L-alanyl-D-glutamate: meso-diaminopimelate ligase (MurE) | murE | 6.3.2.13 | AAC73196.1 |
| putrescine/cadaverine aminopropyltransferase (SpeE) | speE | 2.5.1.16 | AAC73232.1 |
| spermidine acetyltransferase (SpeG) | speG | NA | AAC74656.1 |
| glutamate-putrescine/glutamate-cadaverine ligase (PuuA) | puuA | NA | AAC74379.2 |
| putrescine importer (PuuP) | puuP | NA | AAC74378.2 |
| putrescine/cadaverine aminotransferase (YgjG) | ygjG | 2.6.1.82 | AAC76108.3 |

In some embodiments, a host cell is genetically modified to express a lysine decarboxylase, an aspartate kinase, a dihydrodipicolinate synthase, a diaminopimelate decarboxylase, an aspartate semialdehyde dehydrogenase, a dihydropicolinate reductase, and an aspartate transaminase. Additional modifications may also be incorporated into the host cell.

In some embodiments, a host cell may be genetically modified to attenuate or reduce the expression of one or more polypeptides that affect lysine biosynthesis. Examples of such polypeptides include the *E. coli* genes Pck, Pgi, DeaD, CitE, MenE, PoxB, AceA, AceB, AceE, RpoC, and ThrA, or the corresponding genes from other organisms. Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes attenuated to increase cadaverine production. Illustrative genes encoding polypeptides whose attenuation increases lysine biosynthesis are provided below.

| Protein | Gene | EC Number | GenBank Accession No. |
| --- | --- | --- | --- |
| PEP carboxykinase (Pck) | pck | 4.1.1.49 | NP_417862 |
| Glucose-6-phosphate isomerase (Pgi) | pgi | 5.3.1.9 | NP_418449 |
| DEAD-box RNA helicase (DeaD) | deaD | | NP_417631 |
| citrate lyase (CitE) | citE | 4.1.3.6/ 4.1.3.34 | NP_415149 |
| o-succinylbenzoate-CoA ligase (MenE) | menE | 6.2.1.26 | NP_416763 |
| pyruvate oxidase (PoxB) | poxB | 1.2.2.2 | NP_415392 |
| isocitrate lyase (AceA) | aceA | 4.1.3.1 | NP_418439 |
| malate synthase A (AceB) | aceB | 2.3.3.9 | NP_418438 |
| pyruvate dehydrogenase (aceE) | aceE | 1.2.4.1 | NP_414656 |
| RNA polymerase b' subunit (RpoC) | rpoC | 2.7.7.6 | NP_418415 |
| aspartokinase I (ThrA) | thrA | 2.7.2.4/ 1.1.1.3 | NP_414543 |

Nucleic acids encoding a lysine decarboxylase or a lysine biosynthesis polypeptide may be introduced into the host cell along with a polynucleotide encoding the CsrB or CsrC sRNA, e.g., encoded on a single expression vector, or introduced in multiple expression vectors at the same time. Alternatively, the host cell may be genetically modified to overexpress lysine decarboxylase or one or more lysine biosynthesis polypeptides before or after the host cell is genetically modified to overexpress the CsrB or CsrC sRNA.

In alternative embodiments, a host cell that overexpresses a naturally occurring CsrB or CsrC sRNA can be obtained by other techniques, e.g., by mutagenizing cells, e.g., *E. coli* cells, and screening cells to identify those that express a CsrB or CsrC sRNA, at a higher level compared to the cell prior to mutagenesis.

A host cell a CsrB or CsrC sRNA as described herein is a bacterial host cell. In typical embodiments, the bacterial host cell is a Gram-negative bacterial host cell. In some embodiments of the invention, the bacterium is an enteric bacterium. In some embodiments of the invention, the bacterium is a species of the genus *Corynebacterium, Escherichia, Pseudomonas, Zymomonas, Shewanella, Salmonella, Shigella, Enterobacter, Citrobacter, Cronobacter, Erwinia, Serratia, Proteus, Hafnia, Yersinia, Morganella, Edwardsiella*, or *Klebsiella* taxonomical classes. In some embodiments, the host cells are members of the genus *Escherichia, Hafnia*, or *Corynebacterium*. In some embodiments, the host cell is an *Escherichia coli, Hafnia alvei*, or *Corynebacterium glutamicum* host cell.

In some embodiments, the host cell is a gram-positive bacterial host cell, such as a *Bacillus* sp., e.g., *Bacillus subtilis* or *Bacillus licheniformis*; or another *Bacillus* sp. such as *B. alcalophilus, B. aminovorans, B. amyloliquefaciens, B. caldolyticus, B. circulans, B. stearothermophilus, B. thermoglucosidasius, B. thuringiensis* or *B. vulgatis*.

Host cells modified in accordance with the invention can be screened for increased production of lysine or a lysine derivative, such as cadaverine, as described herein.

Methods of Producing Lysine or a Lysine Derivative.

A host cell genetically modified to overexpress CsrB or CsrC sRNA can be employed to produce lysine or a derivative of lysine. In some embodiments, the host cell produces cadaverine. To produce lysine or the lysine derivative, a host cell genetically modified to overexpress CsrB or CsrC sRNA as described herein can be cultured under conditions suitable to allow expression of the CsrB or CsrC sRNA and expression of enzymes that are used to produce lysine or the lysine derivative. A host cell modified in accordance with the invention provides a higher yield of lysine or lysine derivatives relative to a non-modified counterpart host cell that expresses a CsrB or CsrC sRNA at native levels.

Host cells may be cultured using well known techniques (see, e.g., the illustrative conditions provided in the examples section).

The lysine or lysine derivative can then be separated and purified using known techniques. Lysine or lysine derivatives, e.g., cadaverine, produced in accordance with the invention may then be used in any known process, e.g., to produce a polyamide.

In some embodiments, lysine may be converted to caprolactam using chemical catalysts or by using enzymes and chemical catalysts.

The present invention will be described in greater detail by way of specific examples. The following examples are offered for illustrative purposes, and are not intended to limit the invention in any manner. Those of skill in the art will readily recognize a variety of noncritical parameters, which can be changed or modified to yield essentially the same results.

EXAMPLES

The following examples are offered to illustrate, but not to limit the claimed invention.

Example 1: Construction of Plasmid Vectors that Encode CadA

A plasmid vector containing wild-type *E. coli* cadA (SEQ ID NO: 1), which encodes the lysine decarboxylase CadA (SEQ ID NO: 2), was amplified from the *E. coli* MG1655 K12 genomic DNA using the PCR primers cadA-F and cadA-R, digested using the restriction enzymes SacI and BamHI, and ligated into pSTV28 to generate the plasmid pCIB39. The 5' sequence upstream of the cadA gene was optimized using the PCR primers cadA-F2 and cadA-R2 to create pCIB40. The SacI restriction site was added back to pCIB40 using the SacI-F and SacI-R primers to create pCIB41.

Example 2: Construction of a Plasmid Vector Expressing Genes Encoding CsrA or CsrD The *E. coli* gene, csrA (SEQ ID NO: 3), that encodes a carbon storage regulator, CsrA (SEQ ID NO: 4), was amplified from the *E. coli* MG1655 K12 genomic DNA using the PCR primers csrA-F and csrA-R, digested with the restriction enzymes SacI and BamHI, and ligated into pCIB41 plasmid vector also digested with SacI and BamHI to create pCIB49. Similarly, csrD (SEQ ID NO: 5), that encodes CsrD (SEQ ID NO: 6), was amplified from the *E. coli* MG1655 K12 genomic DNA using the PCR primers csrD-F and csrD-R, the BamHI restriction site was removed using sewing PCR with the primers rmvBamHI-F and rmvBamHI-R, digested with the restriction enzymes SacI and BamHI, and ligated into pCIB41 plasmid vector also digested with SacI and BamHI to create pCIB50.

Example 3: Construction of Plasmid Vectors Co-Expressing Synthetic Operon I that Contains Three Proteins (LysC, DapA, LysA) from the Lysine Biosynthetic Pathway Three genes from *E. coli*, lysC, dapA, and lysA, encode proteins involved in the *E. coli* lysine biosynthetic pathway: aspartate kinase (LysC or AKIII, encoded by lysC), dihydrodipicolinate synthase (DapA or DHDPS, encoded by dapA), and diaminopimelate decarboxylase (LysA, encoded by lysA). The three genes were cloned into a plasmid vector and the three proteins, LysC (SEQ ID NO: 7), DapA (SEQ ID NO: 8), and LysA (SEQ ID NO: 9) were overexpressed in *E. coli*. The gene lysC was amplified from the *E. coli* MG1655 K12 genomic DNA using the primers lysC-F and lysC-R, and the amplified fragment was digested using SacI and BamHI, and ligated into pUC18 to create pCIB7. The gene dapA was amplified from the *E. coli* MG1655 K12 genomic DNA using the primers dapA-F and dapA-R, and the amplified fragment was digested using BamHI and XbaI, and ligated into pCIB7 to create pCIB8. The gene lysA was amplified from the *E. coli* MG1655 K12 genomic DNA using the primers lysA-F and lysA-R, and the amplified fragment was digested using XbaI and SalI, and ligated into pCIB8 to create pCIB9. The three-gene operon was amplified from pCIB9 using the primers lysC-F and lysA-R. The amplified product was digested using SacI and SalI, and the digested fragment was ligated into pCIB10 to create pCIB32.

Example 4: Construction of Plasmid Vectors Co-Expressing Various Aspartokinases. Various Aspartokinases were Expressed in Order to Increase Lysine Production Two pairs of mutations were chosen that enabled the *E. coli* LysC to have an increased feedback resistance to lysine. The gene encoding the first mutant, LysC-1 (M318I, G323D) (SEQ. ID NO: 10) was constructed using the primers 318-F, 318-R, 323-F, 323-R. The genes encoding LysC-1 (M318I, G323D) was cloned into pCIB32 and replaced the wild-type *E. coli* aspartokinase, LysC, to create the plasmids pCIB43. The aspartokinase from *Streptomyces* strains that is capable of producing polylysine was previously suggested, but not proven, to be more feedback resistant to lysine compared to *E. coli* aspartokinase. As such, the aspartokinase gene from *Streptomyces lividans* was codon optimized, synthesized, and cloned in place of wild-type lysC in pCIB32 in order to create the plasmid pCIB55 using the primers SlysC-F and SlysC-R. The resulting aspartokinase protein that was expressed was named S-LysC (SEQ ID NO: 11).

Example 5: Construction of Plasmid Vectors Co-Expressing Synthetic Operon II that Contains Three Proteins (Asd, DapB, DapD, AspC) from the Lysine Biosynthetic Pathway Next, the expression of four additional genes, asd, dapB, dapD, and aspC, which are involved in the lysine biosynthetic pathway of *E. coli*, was enhanced. These genes encode the following enzymes: aspartate semialdehyde dehydrogenase (Asd (SEQ ID NO: 12), encoded by asd), dihydrodipicolinate reductase (DapB or DHDPR (SEQ ID NO: 13), encoded by dapB), tetrahydrodipicolinate succinylase (DapD (SEQ ID NO: 14), encoded by dapD), and aspartate transaminase (AspC (SEQ ID NO: 15), encoded by aspC). The gene asd was amplified from the *E. coli* MG1655 K12 genomic DNA using the primers asd-F and asd-R, and the amplified fragment was digested using SacI and BamHI, and ligated into pUC18 to create pCIB12. The gene dapB was amplified from the *E. coli* MG1655 K12 genomic DNA using the primers dapB-F and dapB-R, and the amplified fragment was digested using BamHI and XbaI, and ligated into pCIB12 to create pCIB13. The gene dapD was amplified from the *E. coli* MG1655 K12 genomic DNA using the primers dapD-F and dapD-R, and the amplified fragment was digested using XbaI and SalI, and ligated into pCIB13 to create pCIB14. Similarly, the gene aspC was amplified from the *E. coli* MG1655 K12 genomic DNA using the primers aspC-F and aspC-R, and the amplified fragment was digested using XbaI and SalI, and ligated into pCIB13 to create pCIB31.

Example 6: Construction of Plasmid Vectors Co-Expressing Synthetic Operons I and II that Contain Proteins from the Lysine Biosynthetic Pathway Synthetic Operon I was further optimized using primers lysC-rbs2-F and lysC-rbs2-R to modify pCIB43 and create the plasmid pCIB378. Synthetic Operon II was further optimized using the primers asd-rbs2-F and asd-rbs2-R to modify pCIB31 and create the plasmid pCIB380. pCIB380 was further modified using the primers SacI-F2, SacI-R2, ApaI-F, and ApaI-R in order to add the restriction enzyme sites for ApaI and SacI to pCIB380 in order to create the plasmid pCIB393. The two synthetic operons, Synthetic Operon I and Synthetic Operon II, consisting of the genes lysC, dapA, lysA, asd, dapB, and aspC were combined into a single vector. The operon from pCIB378 consisting of the genes lysC, dapA, and lysA was amplified using the primers LAL2-SacI-F and LAL2-ApaI-R, digested using the restriction enzymes SacI and ApaI, and ligated into pCIB393 in order to create the plasmid pCIB394.

Example 7: Mutation of E. coli Using Atmospheric and Room Temperature Plasma E. coli MG1655 K12 was mutagenized using the atmospheric and room temperature plasma method (ARTP) (Zhang et al., Appl. Microbiol. Biotechnol. 98: 5387-5396, 2014). The ARTP II-S instrument was purchased from WuXi TMAXTREE Biotechnoogy Co., Ltd. An overnight culture of cells was inoculated into fresh LB medium and grown to an OD of 0.6, after which the cells were treated with plasma for 50, 70, and 90 sec. Each of the three samples were washed and diluted with CGXII media (Keilhauer et al., J. Bacteriol. 175: 5595-5603, 1993).

Example 8: Selection of Mutated E. coli that Show Resistance to S-(β-Aminoethyl)l-Cysteine Each sample of mutagenized E. coli MG1655 K12 was plated on LB agar plates containing 0, 100, 200, 400, 600, 1000, or 2000 mg/L of S-(β-aminoethyl)l-cysteine (AEC). The cells were grown at 37° C. for 2 days, after which the number of colonies growing on each plate was counted. After multiple rounds of ARTP mutagenesis and screening on LB agar plates containing AEC, it was possible to obtain colonies that were able to grow on plates containing 2000 mg/L AEC.

Example 9: Production of Lysine by Mutant E. coli Created Using ARTP

Colonies able to grow on 2000 mg/L AEC were assayed for their lysine production ability. Each colony was grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, and 0.005% L-isoleucine. The following day, each culture was inoculated into 100 mL of fresh medium with 30 g/L of glucose instead and 0.7% $Ca(HCO_3)_2$. The culture was grown for 72 hours at 37° C., at which point the concentration of lysine in each culture was determined (Table 1).

TABLE 1

Production of lysine by E. coli strains mutated using ARTP.

| Strain | Lysine (g/L) |
|---|---|
| MG1655 | n.d. |
| M3 | 2.6 ± 0.2 |
| M4 | 1.8 ± 0.2 |
| M7 | 1.6 ± 0.2 |
| M11 | 2.8 ± 0.2 |
| M15 | 2.3 ± 0.4 |

As shown in Table 1, all of the mutants selected from the LB plates containing AEC demonstrated the ability to overproduce lysine. Specifically, mutants M3, M11, and M15 were able to produce >2.0 g/L.

Example 10: Production of Lysine from Mutant E. coli Over-Expressing Synthetic Operons I and II and CsrA or CsrD E. coli mutant M11 was transformed with one of the following combination of plasmids: pCIB394 and pSTV28, pCIB394 and pCIB49, or pCIB394 and pCIB50. Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, ampicillin (100 μg/mL), and chloramphenicol (20 μg/mL). The following day, each culture was inoculated into 100 mL of fresh medium with 30 g/L of glucose, 0.7% $Ca(HCO_3)_2$, ampicillin (100 μg/mL), and chloramphenicol (20 μg/mL). The culture was grown for 72 hours at 37° C., at which point the concentration of lysine in each culture was determined (Table 2).

TABLE 2

Production of lysine by mutant E. coli M11 containing Synthetic Operons I and II, and CsrA or CsrD.

| Plasmids | Protein(s) | Lysine (g/L) |
|---|---|---|
| pCIB394 & pSTV28 | LysC, DapA, LysA, Asd, DapB, AspC | 7.0 ± 0.2 |
| pCIB394 & pCIB49 | LysC, DapA, LysA, Asd, DapB, AspC, CsrA | 6.3 ± 0.2 |
| pCIB394 & pCIB50 | LysC, DapA, LysA, Asd, DapB, AspC, CsrD | 6.9 ± 0.3 |

As shown in Table 2, the overproduction of CsrA or CsrD did not lead to an increase in lysine production. Surprisingly, the increased expression of csrA led to a decrease in lysine production.

Example 11: Construction of Plasmid Vectors Expressing the sRNAs CsrB or CsrC The E. coli csrB (SEQ ID NO: 16) that encodes CsrB was amplified from the E. coli MG1655 K12 genomic DNA using the PCR primers csrB-F and csrB-R, digested with the restriction enzymes SacI and BamHI, and ligated into pCIB41 plasmid vector also digested with SacI and BamHI to create pCIB51. Similarly, csrC (SEQ ID NO: 17) was amplified from the E. coli MG1655 K12 genomic DNA using the PCR primers csrC-F and csrC-R, digested with the restriction enzymes SacI and BamHI, and ligated into pCIB41 plasmid vector also digested with SacI and BamHI to create pCIB52.

Example 12: Production of Lysine from E. coli Over-Expressing Synthetic Operons I and II and CsrB or CsrC E. coli mutant M11 was transformed with one of the following combination of plasmids: pCIB394 and pSTV28, pCIB394 and pCIB51, or pCIB394 and pCIB52. Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, ampicillin (100 µg/mL), and chloramphenicol (20 µg/mL). The following day, each culture was inoculated into 100 mL of fresh medium with 30 g/L of glucose, 0.7% $Ca(HCO_3)_2$, ampicillin (100 µg/mL), and chloramphenicol (20 µg/mL). The culture was grown for 72 hours at 37° C., at which point the concentration of lysine in each culture was determined (Table 3).

TABLE 3

Production of lysine by mutant E. coli M11 containing Synthetic Operons I and II, and CsrB or CsrC.

| Plasmids | Protein(s) | Lysine (g/L) |
|---|---|---|
| pCIB394 & pSTV28 | LysC, DapA, LysA, Asd, DapB, AspC | 6.8 ± 0.2 |
| pCIB394 & pCIB49 | LysC, DapA, LysA, Asd, DapB, AspC, CsrB | 7.5 ± 0.2 |
| pCIB394 & pCIB50 | LysC, DapA, LysA, Asd, DapB, AspC, CsrC | 7.6 ± 0.2 |

As shown in Table 3, the overproduction of CsrB or CsrC led to an increase in lysine production compared to the control (7.5 or 7.6 g/L compared to 6.8 g/L).

Example 13: Construction of Plasmid Vectors Encoding a Lysine Decarboxylase and CsrB or CsrC The csrB sRNA on pCIB51 was amplified using the primers csrB-F2 and csrB-R2, the amplified fragment was digested using the restriction enzymes BamHI and SphI, and ligated into pCIB41 to form the plasmid pCIB104. Similarly, the csrC sRNA was amplified using the primers csrC-F2 and csrC-R2, the amplified fragment was digested using the restriction enzymes BamHI and SphI, and ligated into pCIB41 to form the plasmid pCIB105.

Example 14: Production of Lysine from E. coli Co-Overexpressing Genes that Encode a Lysine Decarboxylase, CsrB or CsrC, and Lysine Synthetic Operons I and II E. coli MG1655 K12 was transformed with one of the following combination of plasmids: pCIB394 and pSTV28, pCIB394 and pCIB41, pCIB394 and pCIB104, or pCIB394 and pCIB105. Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, ampicillin (100 µg/mL), and chloramphenicol (20 µg/mL). The following day, each culture was inoculated into 100 mL of fresh medium with 30 g/L of glucose, 0.7% $Ca(HCO_3)_2$, ampicillin (100 µg/mL), and chloramphenicol (20 µg/mL). The culture was grown for 72 hours at 37° C., at which point the concentration of lysine and cadaverine in each culture was determined (Table 4).

TABLE 4

Production of lysine and cadaverine by E. coli strains that contain the lysine Synthetic Operons I and II and overproduce a lysine decarboxylase and an imine/enamine deaminase.

| Plasmids | Protein(s) | Lysine (g/L) | Cadaverine (g/L) |
|---|---|---|---|
| pCIB394 & pSTV28 | LysC, DapA, LysA, Asd, DapB, AspC | 7.0 ± 0.2 | n.d. |
| pCIB394 & pCIB41 | LysC, DapA, LysA, Asd, DapB, AspC, CadA | 0.5 ± 0.2 | 3.2 ± 0.2 |
| pCIB394 & pCIB104 | LysC, DapA, LysA, Asd, DapB, AspC, CadA, CsrB | 0.5 ± 0.2 | 3.8 ± 0.2 |
| pCIB394 & pCIB105 | LysC, DapA, LysA, Asd, DapB, AspC, CadA, CsrC | 0.5 ± 0.2 | 3.8 ± 0.2 |

As shown in Table 4, overproduction of CadA led to the production of cadaverine. Furthermore, the overproduction of the sRNA CsrB or CsrC further increased cadaverine production from 3.2 g/L to 3.8 g/L for CsrB and CsrC.

Although the foregoing invention has been described in some detail by way of illustration and example for purposes of clarity of understanding, one of skill in the art will appreciate that certain changes and modifications may be practiced within the scope of the appended claims. All publications, patents, accession numbers, and patent applications cited herein are incorporated herein by reference to disclose and describe the methods and/or materials in connection with which the publications are cited. Where a conflict exists between the instant application and a reference provided herein, the instant application shall dominate.

| Table of plasmids used in Examples | |
|---|---|
| Protein(s)/sRNA Overexpressed | Plasmid |
| none | pSTV28 |
| CadA | pCIB41 |
| CsrA | pCIB49 |
| CsrD | pCIB50 |
| CsrB | pCIB51 |
| CsrC | pCIB52 |
| LysC, DapA, LysA, Asd, DapB, AspC | pCIB394 |
| CadA, CsrB | pCIB104 |
| CadA, CsrC | pCIB105 |

| Table of primer sequences used in Examples. | |
|---|---|
| Name | Sequence (5'-3') |
| cadA-F | ggcgagctcacacaggaaacagaccatgaacgttattgcaatattgaatc |
| cadA-R | ggcggatccccacttcccttgtacgagctaattattattgctttcttctttc |
| cadA-F2 | atttcacacaggaaacagctatgaacgttattgcaatattgaatcac |

-continued

Table of primer sequences used in Examples.

| Name | Sequence (5'-3') |
|---|---|
| cadA-R2 | agctgtttcctgtgtgaaat |
| SacI-F | ggcgagctcctcctgtgtgaaattgttatccgctc |
| SacI-R | ggcgagctcatgaacgttattgcaatattgaatc |
| csrA-F | ggcgagctcatgctgattctgactcgtcg |
| csrA-R | ggcggatccttagtaactggactgctgggat |
| csrD-F | ggcgagctcatgagattaacgacgaaattttcg |
| csrD-R | ggcggatccttaaaccgagtatctttgtgaatat |
| rmvBamHI-F | gtttatcaggacccgatgggca |
| rmvBamHI-R | tgcccatcgggtcctgataaac |
| lysC-F | ggcgagctcacacaggaaacagaccatgtctgaaattgttgtctcc |
| lysC-R | ggcggatccttactcaaacaaattactatgcag |
| dapA-F | ggcggatccacacaggaaacagaccatgttcacgggaagtattgtc |
| dapA-R | ggctctagattacagcaaaccggcatgc |
| lysA-F | ggctctagaacacaggaaacagaccatgccacattcactgttcagc |
| lysA-R | ggcgtcgacttaaagcaattccagcgccag |
| 318-F | cagcctgaatatactgcattctc |
| 318-R | gagaatgcagtatattcaggctg |
| 323-F | gcattctcgcgatttcctcg |
| 323-R | cgaggaaatcgcgagaatgc |
| SlysC-F | ggcgagctcacacaggaaacagaccatgggcttagttgtgcagaaa |
| SlysC-R | ggcggatccttaacgacctgtgccgccata |
| asd-F | ggcgagctcacacaggaaacagaccatgaaaaatgttggttttatcgg |
| asd-R | ggcggatccttacgccagttgacgaagc |
| dapB-F | ggcacacaggaaacagaccatgcatgatgcaaacatccg |
| dapB-R | ggctctagattacaaattattgagatcaagtacatctc |
| dapD-F | ggctctagaacacaggaaacagaccatgcagcagttacagaacat |
| dapD-R | ggcgcatgcttagtcgatggtacgcagca |
| aspC-F | ggctctagaacacaggaaacagaccatgtttgagaacattaccgcc |
| aspC-R | ggcgcatgcgacctcgaggtagtcgacttacagcactgccacaatcg |
| lysC-rbs2-F | atttcacacaggaaacagctatgtctgaaattgttgtctcca |
| lysC-rbs2-R | agctgtttcctgtgtgaaat |
| asd-rbs2-F | atttcacacaggaaacagctatgaaaaatgttggttttatcggctg |
| asd-rbs2-R | agctgtttcctgtgtgaaat |
| SacI-F2 | ggcgagctctcccctgattctgtggataa |
| SacI-R2 | ggcgagctcagcaaaaggccaggaaccgt |
| ApaI-F | ggcgggcccgtattaccgcctttgagtgag |
| ApaI-R | ggcgggcccacagaatcaggggagagctc |
| LAL2-SacI-F | ggcgagctcgttggccgattcattaatgc |

Table of primer sequences used in Examples.

| Name | Sequence (5'-3') |
|---|---|
| LAL2-ApaI-R | ggcgggcccttaaagcaattccagcgccag |
| csrB-F | ggcgagctcgagtcagacaacgaagtgaac |
| csrB-R | ggcggatccaataaaaaaagggagcactgtattc |
| csrC-F | ggcgagctcatagagcgaggacgctaacag |
| csrC-R | ggcggatccaagaaaaaaggcgacagattactc |
| csrB-F2 | ggcggatcccacacaggaggagctcgagtc |
| csrB-R2 | ggcgcatgcaataaaaaaagggagcactgtattc |
| csrC-F2 | ggcggatcccacacaggaggagctcatagag |
| csrC-R2 | ggcgcatgcaagaaaaaaggcgacagattactc |

Illustrative sequences

SEQ ID NO: 1 Escherichia coli cadA nucleic acid sequence
ATGAACGTTATTGCAATATTGAATCACATGGGGGTTTATTTTAAAGAAGAACCCATC
CGTGAACTTCATCGCGCGCTTGAACGTCTGAACTTCCAGATTGTTTACCCGAACGAC
CGTGACGACTTATTAAAACTGATCGAAAACAATGCGCGTCTGTGCGGCGTTATTTTT
GACTGGGATAAATATAATCTCGAGCTGTGCGAAGAAATTAGCAAAATGAACGAGAA
CCTGCCGTTGTACGCGTTCGCTAATACGTATTCCACTCTCGATGTAAGCCTGAATGA
CCTGCGTTTACAGATTAGCTTCTTTGAATATGCGCTGGGTGCTGCTGAAGATATTGCT
AATAAGATCAAGCAGACCACTGACGAATATATCAACACTATTCTGCCTCCGCTGACT
AAAGCACTGTTTAAATATGTTCGTGAAGGTAAATATACTTTCTGTACTCCTGGTCAC
ATGGGCGGTACTGCATTCCAGAAAAGCCCGGTAGGTAGCCTGTTCTATGATTTCTTT
GGTCCGAATACCATGAAATCTGATATTTCCATTTCAGTATCTGAACTGGGTTCTCTGC
TGGATCACAGTGGTCCACACAAAGAAGCAGAACAGTATATCGCTCGCGTCTTTAAC
GCAGACCGCAGCTACATGGTGACCAACGGTACTTCCACTGCGAACAAAATTGTTGGT
ATGTACTCTGCTCCAGCAGGCAGCACCATTCTGATTGACCGTAACTGCCACAAATCG
CTGACCCACCTGATGATGATGAGCGATGTTACGCCAATCTATTTCCGCCCGACCCGT
AACGCTTACGGTATTCTTGGTGGTATCCCACAGAGTGAATTCCAGCACGCTACCATT
GCTAAGCGCGTGAAAGAAACACCAAACGCAACCTGGCCGGTACATGCTGTAATTAC
CAACTCTACCTATGATGGTCTGCTGTACAACACCGACTTCATCAAGAAAACACTGGA
TGTGAAATCCATCCACTTTGACTCCGCGTGGGTGCCTTACACCAACTTCTCACCGATT
TACGAAGGTAAATGCGGTATGAGCGGTGGCCGTGTAGAAGGGAAAGTGATTTACGA
AACCCAGTCCACTCACAAACTGCTGGCGGCGTTCTCTCAGGCTTCCATGATCCACGT
TAAAGGTGACGTAAACGAAGAAACCTTTAACGAAGCCTACATGATGCACACCACCA
CTTCTCCGCACTACGGTATCGTGGCGTCCACTGAAACCGCTGCGGCGATGATGAAAG
GCAATGCAGGTAAGCGTCTGATCAACGGTTCTATTGAACGTGCGATCAAATTCCGTA
AAGAGATCAAACGTCTGAGAACGGAATCTGATGGCTGGTTCTTTGATGTATGGCAGC
CGGATCATATCGATACGATCGAATGCTGGCCGTCTGCGTTCTGACAGCACCTGGCAC
GCTTCAAAAACATCGATAACGAGCACATGTATCTTGACCCGATCAAAGTCACCCTGC
TGACTCCGGGGATGGAAAAAGACGGCACCATGAGCGACTTTGGTATTCCGGCCAGC
ATCGTGGCGAAATACCTCGACGAACATGGCATCGTTGTTGAGAAAACCGGTCCGTAT
AACCTGCTGTTCCTGTTCAGCATCGGTATCGATAAGACCAAAGCACTGAGCCTGCTG
CGTGCTCTGACTGACTTTAAACGTGCGTTCGACCTGAACCTGCGTGTGAAAAACATG
CTGCCGTCTCTGTATCGTGAAGATCCTGAATTCTATGAAAACATGCGTATTCAGGAA
CTGGCTCAGAATATCCACAAACTGATTGTTCACCACAATCTGCCGGATCTGATGTAT
CGCGCATTTGAAGTGCTGCCGACGATGGTAATGACTCCGTATGCTGCATTCCAGAAA
GAGCTGCACGGTATGACCGAAGAAGTTTACCTCGACGAAATGGTAGGTCGTATTAA
CGCCAATATGATCCTTCCGTACCCGCCGGGAGTTCCTCTGGTAATGCCGGGTGAAAT
GATCACCGAAGAAAGCCGTCCGGTTCTGGAGTTCCTGCAGATGCTGTGTGAAATCGG
CGCTCACTATCCGGGCTTTGAAACCGATATTCACGGTGCATACCGTCAGGCTGATGG
CCGCTATACCGTTAAGGTATTGAAAGAAGAAAGCAAAAATAA SEQ ID NO: 2 CadA polypeptide sequence
MNVIAILNHMGVYFKEEPIRELEIRALERLNFQIVYPNDRDDLLKLIENNARLCGVIFDWD
KYNLELCEEISKMNENLPLYAFANTYSTLDVSLNDLRLQISFFEYALGAAEDIANKIKQT
TDEYINTILPPLTKALFKYVREGKYTFCTPGEIMGGTAFQKSPVGSLFYDFFGPNTMKSDI
SISVSELGSLLDHSGPEIKEAEQYIARVFNADRSYMVTNGTSTANKIVGMYSAPAGSTILI
DRNCHKSLTELMMMSDVTPIYFRPTRNAYGILGGIPQSEFQHATIAKRVKETPNATWPV
HAVITNSTYDGLLYNTDFIKKTLDVKSIHFDSAWVPYTNFSPIYEGKCGMSGGRVEGKVI
YETQSTHKLLAAFSQASMIHVKGDVNEETFNEAYMMHTTTSPHYGIVASIETAAAMMK
GNAGKRLINGSIERAIKFRKEIKRLRIESDGWFFDVWQPDHIDTIECWPLRSDSTWHGFK
NIDNEHMYLDPIKVTLLTPGMEKDGTMSDFGIPASIVAKYLDEHGIVVEKTGPYNLLFLF
SIGIDKTKALSLLRALTDFKRAFDLNLRVKNMLPSLYREDPEFYENMRIQELAQNIHKLI

| Illustrative sequences |
|---|
| VEIHNLPDLMYRAFEVLPTMVMTPYAAFQKELHGMTEEVYLDEMVGRINANMILPYPP
GVPLVMPGEMIIEESRPVLEFLQMLCEIGAHYPGFETDIHGAYRQA
DGRYTVKVLKEESKK SEQ ID NO: 3 *E. coli* csrA nucleic acid sequence
ATGCTGATTCTGACTCGTCGAGTTGGTGAGACCCTCATGATTGGGGATGAGGTCACC
GTGACAGTTTTAGGGGTAAAGGGCAACCAGGTACGTATTGGCGTAAATGCCCCGAA
GGAAGTTTCTGTTCACCGTGAAGAGATCTACCAGCGTATCCAGGCTGAAAAATCCCA
GCAGTCCAGTTACTAA SEQ ID NO: 4 CsrA polypeptide sequence
MLILTRRVGETLMIGDEVTVTVLGVKGNQVRIGVNAPKEVSVEIREEIYQRIQAEKSQQS
SY SEQ ID NO: 5 *E. coli* csrD nucleic acid sequence
ATGAGATTAACGACGAAATTTTCGGCCTTTGTTACGCTGCTCACCGGGTTAACAATT
TTTGTGACTTTGCTGGGCTGTTCGCTAAGTTTCTACAACGCCATTCAGTATAAGTTTA
GTCATCGCGTTCAGGCGGTGGCGACGGCGATTGATACCCACCTTGTGTCGAATGACT
TCAGCGTATTAAGGCCACAAATTACCGAATTAATGATGTCGGCAGATATCGTTCGTG
TAGACCTGCTCCATGGTGATAAACAGGTTTATACCCTGGCCAGAAATGGTAGTTATC
GTCCAGTTGGCTCCAGCGATCTGTTTCGCGAACTGAGCGTTCCGTTGATAAAGCATC
CGGGGATGTCGTTGCGTCTGGTTTATCAGGACCCGATGGGCAACTATTTCCATTCGT
TGATGACCACCGCGCCGCTCACGGGGGCGATTGGCTTTATCATTGTTATGCTCTTCCT
GGCGGTACGCTGGTTACAACGGCAACTTGCCGGGCAAGAATTGCTGGAAACCCGGG
CTACTCGTATCTTAAACGGTGAGCGTGGCTCTAATGTGTTGGGAACCATCTATGAAT
GGCCGCCCAGAACCAGCAGTGCGCTGGATACGCTGCTTCGTGAAATTCAGAACGCA
CGCGAACAACACAGCCGTCTTGATACGCTGATCCGCTCTTATGCCGCCCAGGACGTG
AAAACCGGCCTCAATAACGACTCTTTTTCGATAATCAGTTAGCAACGTTACTGGAA
GATCAGGAGAAAGTAGGTACCCACGGGATCGTGATGATGATTCGTCTGCCGGATTTC
AATATGTTGAGCGATACCTGGGGGCACAGCCAGGTTGAAGAACAGTTCTTCACTCTG
ACGAATCTGCTGTCGACATTTATGATGCGCTACCCTGGCGCACTGCTGGCGCGTTAC
CACCGCAGTGATTTTGCTGCGCTGTTACCGCACCGGACGTTAAAAGAGGCAGAGAG
CATCGCCGGTCAGTTAATCAAAGCCGTTGATACCTTGCCGAACAATAAAATGCTCGA
TCGCGACGATATGATCCACATTGGTATCTGCGCCTGGCGTAGTGGTCAGGATACCGA
GCAGGTAATGGAACATGCAGAGTCTGCCACGCGTAATGCGGGATTGCAGGGCGGCA
ATAGCTGGGCTATTTACGATGACTCGTTGCCTGAAAAAGGACGCGGTAATGTTCGCT
GGCGTACGCTTATCGAGCAAATGCTCAGTCGCGGCGGCCCCGCGCCTTTATCAAAAAC
CGGCGGTTACTCGCGAAGGTCAGGTTCATCATCGCGAACTCATGTGCCGCATCTTCG
ATGGTAATGAAGAGGTTAGCTCGGCGGAGTATATGCCGATGGTCTTGCAGTTTGGCT
TATCGGAAGAGTATGACCGTCTGCAAATCAGCCGTCTTATTCCACTATTGCGTTACT
GGCCAGAGGAAAATCTGGCGATTCAGGTTACCGTTGAGTCGCTGATTCGCCCGCGTT
TTCAGCGTTGGCTGCGCGATACGTTAATGCAATGTGAAAAATCACAACGAAAACGC
ATAATTATTGAACTTGCAGAGGCCGATGTAGGTCAACATATCAGTCGTTTACAACCT
GTTATTCGTTTAGTGAATGCTTTAGGGGTACGGGTAGCCGTCAACCAGGCTGGTTTG
ACGCTGGTAAGTACCAGTTGGATCAAAGAACTTAATGTTGAGTTACTCAAGCTCCAT
CCGGGGCTGGTCAGAAACATTGAGAAGCGAACGGAGAACCAGCTGCTGGTTCAAAG
CCTGGTGGAAGCCTGCTCCGGGACCAGCACCCAGGTTTACGCCACCGGCGTGCGTTC
GCGAAGCGAGTGGCAGACCCTGATTCAGCGCGGTGTTACAGGCGGGCAAGGGGATT
TTTTCGCGTCCTCACAGCCACTTGATACTAACGTGAAAAAATATTCACAAAGATACT
CGGTTTAA SEQ ID NO: 6 CsrD polypeptide sequence
MRLTTKFSAFVTLLTGLTIFVTLLGCSLSFYNAIQYKFSHRVQAVATAIDTHLVSNDFSV
LRPQIIELMMSADIVRVDLLHGDKQVYTLARNGSYRPVGSSDLFRELSVPLIKHPGMSL
RLVYQDPMGNYFHSLMTTAPLTGAIGFIIVMLFLAVRWLQRQLAGQELLETRATRILNG
ERGSNVLGTIYEWPPRTSSALDTLLREIQNAREQHSRLDTLIRSYAAQDVKTGLNNRLFF
DNQLATLLEDQEKVGTHGIVMMIRLPDFNMLSDTWGHSQVEEQFFTLTNLLSTFMMRY
PGALLARYHRSDFAALLPHRTLKEAESIAGQLIKAVDTLPNNKMLDRDDMIHIGICAWR
SGQDTEQVMEHAESATRNAGLQGGNSWAIYDDSLPEKGRGNVRWRTLIEQMLSRGGP
RLYQKPAVTREGQVHHRELMCRIFDGNEEVSSAEYMPMVLQFGLSEEYDRLQISRLIPL
LRYVVPEENLAIQVTVESLIRPRFQRWLRDTLMQCEKSQRKRIIIELAEADVGQIIISRLQPV
IRLVNALGVRVAVNQAGLTLVSTSWIKELNVELLKLHPGLVRNIEKRTENQLLVQSLVE
ACSGTSTQVYATGVRSREWQTLIQRGVTGGQGDFFASSQPLDTNVKKYSQRYSV SEQ ID NO: 7 LysC polypeptide sequence
MSEIVVSKFGGTSVADFPDAMNRSADIVLSDANVRLVVLSASAGITNLLVALAEGLEPGE
RFEKLDAIRNIQFAILERLRYPNVIREEIERLLENITVLAEAAALATSPALTDELVSHGELM
STLLFVEILRERDVQAQWFDVRKVMRTNDRFGRAEPDIAALAELAALQLLPRLNEGLVI
TQGFIGSENKGRTTTLGRGGSDYTAALLAEALHASRVDIWTDVPGIYTTDPRVVSAAKRI
DEIAFAEAAEMATFGAKVLEIPATLLPAVRSDIPVFVGSSKDPRAGGTLVCNKTENPPLFR
ALALRRNQTLLTLHSLNMLHSRGFLAEVFGILARHNISVDLITTSEVSVALTLDTTGSTST
GDTLLTQSLLMELSALCRVEVEEGLALVALIGNDLSKACGVGKEVFGVLEPFNIRMICY
GASSHNLCFLVPGEDAEQVVQKLHSNLFE SEQ ID NO: 8 DapA polypeptide sequence
MFTGSIVMVTPMDEKGNVCRASLKKLIDYHVASGTSMVSVGTTGESATLNEDEHADV
VMMTLDLADGRIPVIAGTGANATAEAISLTQRFNDSGIVGCLTVTPYYNRPSQEGLYQH |

```
FKAIAEHTDLPQILYNVPSRTGCDLLPETVGRLAKVKNIIGIKEATGNLTRVNQIKELVSD
DFVLLSGDDASALDFMQLGGHGVISVTANVAARDMAQMCKLAAEGHFAEARVINQRL
MPLHNKLFVEPNPIPVKWACKELGLVATDTLRLPMTPITDSGRETVRAALKHAGLL

SEQ ID NO: 9 LysA polypeptide sequence
MPHSLFSTDTDLTAENLLRLPAEFGCPVWVYDAQIIRRQIAALKQFDVVRFAQKACSNIH
ILRLMREQGVKVDSVSLGEIERALAAGYNPQTHPDDIVFTADVIDQATLERVSELQIPVN
AGSVDMLDQLGQVSPGEIRVWLRVNPGFGHGHSQKTNTGGENSKHGIWYTDLPAALDV
IQREIHQLVGIEIMEIGSGVDYABLEQVCGAMVRQVIEFGQDLQAISAGGGLSVPYQQG
EEAVDTEHYYGLWNAAREQTAMILGHPVKLEIEPGRFLVAQSGVLITQVRSVKQMGSR
HFVLVDAGFNDLMRPAMYGSYEHISALAADGRSLEHAPTVETVVAGPLCESGDVFTQQ
EGGNVETRALPEVKAGDYLVLEIDTGAYGASMSSNYNSRPLLPEVLFDNGQARLIRRRQ
TIEELLALELL SEQ ID NO: 10 LysC-1 M318I, G323D polypeptide sequence
MSEIVVSKFGGTSVADFDAMNRSADIVLSDANVRLVVLSASAGITNLLVALAEGLEPGE
RFEKLDAIRNIQFAILERLRYPNVIREEIERLLENITVLAEAAALATSPALTDELVSHGELM
STLLEVEILRERDVQAQWEDVRKVMRTNDRFGRAEPDIAALAELAALQLLPRLNEGLVI
TQGFIGSENKGRTTTLGRGGSDYTAALLAEALHASRVDIWTDVPGIYTTDPRVVSAAKRI
DEIAFAEAAEMATFGAKVLEIPATLLPAVRSDIPVFVGSSKDPRAGGTLVCNKTENPPLFR
ALALRRNQTLLTLHSLNILHSRDFLAEVFGILARHNISVDLITTSEVSVALTLDTTGSTSTG
DTLLTQSLLMELSALCRVEVEEGLALVALIGNDLSKACGVGKEVFGVLEPFNIRMICYG
ASSHNLCFLVPGEDAEQVVQKLHSNLFE SEQ ID NO: 11 S-LysC polypeptide sequence
MGLVVQKYGGSSVADAEGIKRVAKRIVEAKKNGNQVVAVVSAMGDTTDELIDLAEQV
SPIPAGRELDMLLTAGERISMALLAMAIKNLGHEAQSFTGSQAGVITDSVHNKARIIDVT
PGRIRTSVDEGNVAIVAGFQGVSQDSKDITTLGRGGSDTTAVALAAALDADVCEIYTDV
DGVFTADPRVVPKAKKIDWISEEDMLELAASGSKVLLEIRCVEYARRYNIPIHVRSSFSGL
QGTWVSSEPIKQGEKHVEQALISGVAHDTSEAKVTVVGVPDKPGEAAAIFRAIADAQVN
IDMVVQNVSAASTGLTDISFTLPKSEGRKAIDALEKNRPGIGFDSLRYDDQIGKISLVGAG
MKSNPGVTADFFTALSDAGVNIELISTSEIRISVVTRKDDVNEAVRAVHTAFGLDSDSE
AVVYGGTGR SEQ ID NO: 12 Asd polypeptide sequence
MKNVGFIGWRGMVGSVLMQRMVEERDFDAIRPVFFSTSQLGQAAPSFGGTTGTLQDAF
DLEALKALDIIVTCQGGDYTNEIYPKLRESGWQGYVVIDAASSLRMKDDAIIILDPVNQDV
ITDGLNNGIRTFVGGNCTVSLMLMSLGGLFANDLVDWVSVATYQAASGGGARHMREL
LTQMGHLYGHVADELATPSSAILDIERKVTTLTRSGELPVDNFGVPLAGSLIPWIDKQLD
NGQSREEWKGQAETNKILNTSSVIPVDGLCVRVGALRCHSQAFTIKLKKDVSIPTVEELL
AAHNPWAKVVPNDREITMRELTPAAVTGTLTTPVGRLRKLNMGPEFLSAFTVGDQ SEQ ID NO: 13 DapB polypeptide sequence
MHDANIRVAIAGAGGRMGRQLIQAALALEGVQLGAALEREGSSLLGSDAGELAGAGKT
GVTVQSSLDAVKDDFDVFIDFTRPEGTLNHLAFCRQHGKGMVIGTTGFDEAGKQAIRDA
AADIAIVFAANFSVGVNVMLKLLEKAAKVMGDYTDIEIMAHEIREIKVDAPSGTALAMG
EAIAHALDKDLKDCAVYSREGHTGERVPGTIGFATVRAGDIVGEHTAMFADIGERLEIT
EIKASSRMTFANGAVRSALWLSGKESGLFDMRDVLDLNNL SEQ ID NO: 14 DapD polypeptide sequence
MQQLQNIIETAFERRAEITPANADTVTREAVNQVIALLDSGALRVAEKIDGQWVTHQWL
KKAVLLSFRINDNQVIEGAESRYFDKVPMKFADYDEARFQKEGFRVVPPAAVRQGAFIA
RNTVLMPSYVNIGAYVDEGTMVDTWATVGSCAQIGKNVEILSGGVGIGGVLEPLQANPT
IIEDNCFIGARSEVVEGVIVEEGSVISMGVYIGQSTRIYDRETGEIHYGRVPAGSVVVSGN
LPSKDGKYSLYCAVIVKKVDAKTRGKVGINELLRTID SEQ ID NO: 15 AspC polypeptide sequence
MFENITAAPADPILGLADLFRADERPGKINLGIGVYKDETGKTPVLTSVKKAEQYLLENE
TTKNYLGIDGIPEFGRCTQELLFGKGSALINDKRARTAQTPGGTGALRVAADFLAKNTS
VKRVWVSNPSWPNEIKSVFNSAGLEVREYAYYDAENHTLDFDALINSLNEAQAGDVVL
FHGCCHNPTGIDPTLEQWQTLAQLSVEKGWLPLFDFAYQGFARGLEEDAEGLRAFAAM
HKELIVASSYSKNFGLYNERVGACTLVAADSETVDRAFSQMKAAIRANYSNPPAHGAS
VVATILSNDALRAIWEQELTDMRQRIQRMRQLFVNTLQEKGANRDFSFIIKQNGMFSFS
GLTKEQVLRLREEFGVYAVASGRVNVAGMTPDNMAPLCEAIVAVL SEQ ID NO: 16 E. coli csrB nucleic acid sequence
GAGTCAGACAACGAAGTGAACATCAGGATGATGACACTTCTGCAGGACACACCAGG
ATGGTGTTTCAGGGAAAGGCTTCTGGATGAAGCGAAGAGGATGACGCAGGACGCGT
TAAAGGACACCTCCAGGATGGAGAATGAGAACCGGTCAGGATGATTCGGTGGGTCA
GGAAGGCCAGGGACACTTCAGGATGAAGTATCACATCGGGGTGGTGTGAGCAGGAA
GCAATAGTTCAGGATGAACGATTGGCCGCAAGGCCAGAGGAAAGTTGTCAAGGAT
GAGCAGGGAGCAACAAAAGTAGCTGGAATGCTGCGAAACGAACCGGGAGCGCTGT
GAATACAGTGCTCCCTTTTTTTATT SEQ ID NO: 17 E. coli csrC nucleic acid sequence
ATAGAGCGGAGGACGCTAACAGGAACAATGACTCAGGATGAGGGTCAGGAGCGCCA
GGAGGCGAAGACAGAGGATTGTCAGGAAGACAAACGTCCGGAGACGTAATTAAAC
```

| Illustrative sequences |
|---|
| GGAAATGGAATCAACACGGATTGTTCCGGCTAAAGGAAAAACAGGGTGTGTTGGCG<br>GCCTGCAAGGATTGTAAGACCCGTTAAGGGTTATGAGTCAGGAAAAAAGGCGACAG<br>AGTAATCTGTCGCCTTTTTTCTT<br><br>SEQ ID NO: 18 *Shigella flexneri* CsrB nucleic acid sequence<br>(CP024470.1)<br>GAGTCAGACAACGAAGTGAACATCAGGATGATGACACTTCTGCAGGACACACCAGG<br>ATGGTGTTTCAGGGAAAGGCTTCTGGATGAAGCGAAGAGGATGACGCAGGACGCGT<br>TAAAGGACACCTCCAGGATGGAGAATGAGAACCGGTCAGGATGATTCGGTGGGTCA<br>GGAAGGCCAGGGACACTTCAGGATGAAGTATCACATCGGGGTGGTGTGAGCAGGAA<br>GCAATAGTTCAGGATGAACGATTGGCCGCAAGGCCAGAGGAAAAGTTGTCAAGGAT<br>GAGCAGGGAGCAACAAAAGTAGCTGGAATGCTGCGAAACGAACCGGGAGCACTGT<br>GAATACAGTGCTCCCTTTTTTATT<br><br>SEQ ID NO: 19 *Triticum aestivum* CsrB nucleic acid sequence<br>(AK447219.1)<br>GAGTCAGACAACGAAGTGAACATCAGGATGATGACACTTCTGCAGGAAACACCAGG<br>ATGGTGTTTCAGGGAAAGGCTTCTGGATGAAGCGAAGAGGATGACGCAGGACGCGT<br>TAAAGGACACCTCCAGGATGGAGAATGAGAACCGGTCAGGATGATTCGGTGGGTCA<br>GGAAGGCCAGGGACACTTCAGGATGAAGTATCACATCGGGGTGGTGTGAGCAGGAA<br>GCAATAGTTCAGGATGAACGATTGGCCGCAAGGCCAGAGGAAAAGTTGTCAAGGAT<br>GAGCAGGGAGCAACAAAAGTAGCTGGAATGCTGCGAAACGAACCGGGAGCGCTGT<br>GAATACAGTGCTCCCTTTTTTATT<br><br>SEQ ID NO: 20 *Shigella sonnei* CsrB nucleic acid sequence<br>(CP023645.1)<br>GAGTCAGACAACGAAGTGAACATCAGGATGATGACACTTCTGCAGGACACACCAGG<br>ATGGTGTTTCAGGGAAAGGCTTCTGGATGAAGCGAAGAGGATGACGCAGGACGCGT<br>TAAAGGACACCTCCAGGATGGAGAATGAGAACCGGTCAGGATGATTCGGTGGGTCA<br>GGAAGGCCAGGGACACTTCAGGATGAAGTATCACATCGGGGTGGTGTGAGCAGGAA<br>GCAATAGTTCAGGATGAACGATTGGCCGCAAGGCCAGAGGAAAAGTTGTCAAGGAT<br>GAGCAGGGAGCAACAAAAGTAGCTGGAATGCTGCGAAACGAACCGGGAGCACTGT<br>GAATACAGTGCTCCCTTTTTTATT<br><br>SEQ ID NO: 21 *Citrobacter* sp. CsrB nucleic acid sequence<br>(LT556085.1)<br>GAGTCGCACAACGAAGTGAACATCAGGATGATGACACTTCAGCAGGACACACCAGG<br>ACGGTGTTACAGGGAAAGGCTTCAGGATGAAGTGAAGAGGATAACGCGGGAATGC<br>GTTAAAGGACACCTCCAGGAAGGAGAACGAGAGCCGGTCAGGATAGTCGGTGGGTC<br>AGGATGGCCAGGATGCTTCAGGATGAAGTAATCACATCGGGGTGGTGTGAGCAGGA<br>TGCAAAATGTTCAGGATGAACAACAGGTCGCAAGACCAGAGGAAAAGTTGTCACGG<br>ATGAGCAGGGAGCACAAAAAGTAGCTGGAATGCTGCGAAACGAACCGGGAGCACT<br>GTTTTTACAGTGCTCCCTTTTTTT<br><br>SEQ ID NO: 22 *Salmonella enterica* subsp. CsrB nucleic acid sequence<br>(CP015574.1)<br>GAGTCGTACAACGAAGCGAACGTCAGGATGATGACGCTTCAGCAGGACACGCCAGG<br>ATGGTGTTACAAGGAAAGGCTTCAGGATGAAGCAAAGTGGAAAGCGCAGGATGCGT<br>TAAAGGACACCTCCAGGACGGAGAACGAGAGCCGATCAGGATGTTCGGCGGGTCTG<br>GATGACCAGGGACGCTTCAGGATGAAGCTATCACATCGGGCGATGTGCGCAGGATG<br>CAAACGTTCAGGATGAACAGGCCGTAAGGTCACAGGAAAAGTTGTCACGGATGAGC<br>AGGGAGCACGAAAAGTAGCTGGAATGCTGCGAAACGAACCGGGAGCACTGTTTATA<br>CAGTGCTCCCTTTTTTT<br><br>SEQ ID NO: 23 *Shigella sonnei* CsrC nucleic acid sequence<br>(CP023645.1)<br>ATAGAGCGAGGACGCTAACAGGAACAATGACTCAGGATGAGGGTCAGGAGCGCCA<br>GGAGGCGAAGACAGAGGATTGTCAGGAAGACAAACGTCCGGAGACGTAATTAAAC<br>GGAAATGGAATCAACACGGATTGTTCCGGCTAAAGGAAAAACAGGGTGTGTTGGCG<br>GCCTGCAAGGATTGTAAGACCCGTTAAGGGTTATGAGTCAGGAAAAAAGGCGACAG<br>AGTAATCTGTCGCCTTTTTTCTT<br><br>SEQ ID NO: 24 *Shigella flexneri* CsrC nucleic acid sequence<br>(CP024470.1)<br>ATAGAGCGAGGACGCTAACAGGAACAATGACTCAGGATGAGGGTCAGGAGCGCCA<br>GGAGGCGAAGACAGAGGATTGTCAGGAAGACAAACGTCCGGAGACGTAATTAAAC<br>GGAAATGGAATCAACACGGATTGTTCCGGCTAATGGAAAAACAGGGTGTGTTGGCG<br>GCCTGCAAGGATTGTAAGACCCGTTAAGGGTTATGAGTCAGGAAAAAAGGCGACAG<br>AGTAATCTGTCGCCTTTTTTCTT<br><br>SEQ ID NO: 25 *Citrobacter werkmaniii* CsrC nucleic acid sequence<br>(CP023504.1)<br>AGCGAGGGAGCTAACAGGATAAACGACTCAGGATGAGGGTCAGGAGCGCCAGGAG<br>GCGAAGACGCAGGATTGTCAGGAAGACAAACGTCCGGAGACGTTAGTAAAAGGAA<br>ATGGAAACAACACGGAATGTTTCTGGCTAAGGGAAAAACAGGGTGTGTTGATAGCC<br>GACAGGGATTGTAGGGCCCGTTAAGGGTTGAGAGTCAGGAAAAAAGGCGACAGATT<br>ACTCTGTCGCCTTTTTTCTT |

-continued

Illustrative sequences

SEQ ID NO: 26 *Salmonella enterica* subsp. CsrC nucleic acid sequence
(CP018661.1)
AGCGAGGACGCTAACAGGATCAACGACTCAGGATGAGGGTCAGGAGCGCCAGGAG
GCGAAGACACAGGATTGTCAGGAAGACAAACGTCCGGAGACGTTAGTAAAAGGAA
ATGGAAACAACATGGAATGTTCCAGGCTAAGGGAAAAACAGGGCGTGTTGATAGCC
AACAGGGATGGTGGAACCCGTTAAGGGTCGTGAGTCAAGAAAAAAGGCGGCAGATT
ACTCTGTCGCCTTTTTTCTT

What is claimed is:

1. A genetically modified host cell comprising an exogenous nucleic acid encoding a CsrB sRNA or a CsrC sRNA, wherein the host cell overexpresses the CsrB sRNA or CsrC sRNA relative to a counterpart host cell that has not been modified to express the exogenous nucleic acid; and overexpresses one or more proteins selected from the group consisting of a lysine decarboxylase, an aspartate kinase, a dihydrodipicolinate synthase, a diaminopimelate decarboxylase, an aspartate semialdehyde dehydrogenase, a dihydropicolinate reductase, and an aspartate transaminase to increase production of lysine or a lysine derivative compared to a wildtype host cell, wherein the host cell is *Escherichia coli*, and wherein the CsrB sRNA comprises a nucleotide sequence having at least 85% identity to SEQ ID NO: 16 and the CsrC sRNA comprises a nucleotide sequence having at least 85% identity to SEQ ID NO: 17.

2. The genetically modified host cell of claim 1, wherein:
   (i) the amino acid derivative is cadaverine; or
   (ii) a CsrB or CsrC is heterologous to the host cell.

3. The genetically modified host cell of claim 1, wherein the CsrB sRNA comprises the nucleic acid sequence of SEQ ID NO:16 and the CsrC sRNA comprises the nucleic acid sequence of SEQ ID NO:17.

4. The genetically modified host cell of claim 1, wherein the exogenous nucleic acid encoding the CsrB or CsrC is encoded by an expression vector introduced into the cell, wherein the expression vector comprises the exogenous nucleic acid operably linked to a promoter, or the exogenous nucleic acid is integrated into the host chromosome.

5. The genetically modified host cell of claim 1, wherein the aspartate kinase, dihydrodipicolinate synthase, diaminopimelate decarboxylase, aspartate semialdehyde dehydrogenase, dihydropicolinate reductase, or aspartate transaminase is a LysC, DapA, LysA, Asd, DapB, or AspC polypeptide.

6. The genetically modified host cell of claim 1, wherein the host cell overexpresses CadA, LysC, DapA, LysA, Asd, DapB, and AspC polypeptide.

7. A method of producing lysine or a lysine derivative, the method comprising culturing a host cell of claim 1 under conditions in which the CsrB sRNA or CsrC sRNA is overexpressed.

8. A method of engineering a host cell to increase production of lysine or a lysine derivative, the method comprising introducing an exogenous nucleic acid encoding a CsrB or CsrC sRNA into the host cell, wherein the host cell overexpresses one or more proteins selected from the group consisting of a lysine decarboxylase, an aspartate kinase, a dihydrodipicolinate synthase, a diaminopimelate decarboxylase, an aspartate semialdehyde dehydrogenase, a dihydropicolinate reductase and an aspartate transaminase to increase production of lysine or a lysine derivative compared to a wildtype host cell;
   culturing the host cell under conditions in which the CsrB or CsrC sRNA is expressed, and
   selecting a host cell that exhibits increased production of lysine or a lysine derivative relative to a counterpart control host cell that has not been modified to express the exogenous nucleic acid, wherein the host cell is *Escherichia coli*, and wherein the CsrB sRNA comprises a nucleotide sequence having at least 85% identity to SEQ ID NO: 16 and the CsrC sRNA comprises a nucleotide sequence having at least 85% identity to SEQ ID NO: 17.

9. The method of claim 8, wherein,
   (i) the amino acid derivative is cadaverine; or
   (ii) the CsrB or CsrC sRNA is heterologous to the host cell.

10. The method of claim 8, wherein the exogenous nucleic acid encoding the CsrB or CsrC sRNA is encoded by an expression vector introduced into the cell, wherein the expression vector comprises the exogenous nucleic acid operably linked to a promoter, or the exogenous nucleic acid is integrated into the host chromosome.

11. The method of claim 8, wherein the aspartate kinase, dihydrodipicolinate synthase, diaminopimelate decarboxylase, aspartate semialdehyde dehydrogenase, dihydropicolinate reductase, or aspartate transaminase is a LysC, DapA, LysA, Asd, DapB, or AspC polypeptide.

12. The method of claim 8, wherein the host cell overexpresses a CadA, LysC, DapA, LysA, Asd, DapB, and AspC polypeptide.

* * * * *

SEQUENCE LISTING

<160> NUMBER OF SEQ ID NOS: 76

<210> SEQ ID NO 1
<211> LENGTH: 2148
<212> TYPE: DNA
<213> ORGANISM: Escherichia coli

<400> SEQUENCE: 1

| | | | | | |
|---|---|---|---|---|---|
| atgaacgtta | ttgcaatatt | gaatcacatg | ggggtttatt | ttaaagaaga | acccatccgt | 60 |
| gaacttcatc | gcgcgcttga | acgtctgaac | ttccagattg | tttacccgaa | cgaccgtgac | 120 |
| gacttattaa | aactgatcga | aaacaatgcg | cgtctgtgcg | gcgttatttt | tgactgggat | 180 |
| aaatataatc | tcgagctgtg | cgaagaaatt | agcaaaatga | acgagaacct | gccgttgtac | 240 |
| gcgttcgcta | atacgtattc | cactctcgat | gtaagcctga | atgacctgcg | tttacagatt | 300 |
| agcttctttg | aatatgcgct | gggtgctgct | gaagatattg | ctaataagat | caagcagacc | 360 |
| actgacgaat | atatcaacac | tattctgcct | ccgctgacta | agcactgtt | taaatatgtt | 420 |
| cgtgaaggta | aatatacttt | ctgtactcct | ggtcacatgg | gcggtactgc | attccagaaa | 480 |
| agcccggtag | gtagcctgtt | ctatgatttc | tttggtccga | ataccatgaa | atctgatatt | 540 |
| tccatttcag | tatctgaact | gggttctctg | ctggatcaca | gtggtccaca | caaagaagca | 600 |
| gaacagtata | tcgctcgcgt | ctttaacgca | gaccgcagct | acatggtgac | caacggtact | 660 |
| tccactgcga | acaaaattgt | tggtatgtac | tctgctccag | caggcagcac | cattctgatt | 720 |
| gaccgtaact | gccacaaatc | gctgacccac | ctgatgatga | tgagcgatgt | tacgccaatc | 780 |
| tatttccgcc | cgaccccgtaa | cgcttacggt | attcttggtg | tatcccaca | gagtgaattc | 840 |
| cagcacgcta | ccattgctaa | gcgcgtgaaa | gaaacaccaa | cgcaacctg | gccggtacat | 900 |
| gctgtaatta | ccaactctac | ctatgatggt | ctgctgtaca | caccgactt | catcaagaaa | 960 |
| acactggatg | tgaaatccat | ccactttgac | tccgcgtggg | tgccttacac | caacttctca | 1020 |
| ccgatttacg | aaggtaaatg | cggtatgagc | ggtggccgtg | tagaagggaa | agtgatttac | 1080 |
| gaaacccagt | ccactcacaa | actgctggcg | gcgttctctc | aggcttccat | gatccacgtt | 1140 |
| aaaggtgacg | taaacgaaga | aacctttaac | gaagcctaca | tgatgcacac | caccacttct | 1200 |
| ccgcactacg | gtatcgtggc | gtccactgaa | accgctgcgg | cgatgatgaa | aggcaatgca | 1260 |
| ggtaagcgtc | tgatcaacgg | ttctattgaa | cgtgcgatca | aattccgtaa | agagatcaaa | 1320 |
| cgtctgagaa | cggaatctga | tggctggttc | tttgatgtat | ggcagccgga | tcatatcgat | 1380 |
| acgactgaat | gctggccgct | gcgttctgac | agcacctggc | acggcttcaa | aaacatcgat | 1440 |
| aacgagcaca | tgtatcttga | cccgatcaaa | gtcaccctgc | tgactccggg | gatggaaaaa | 1500 |
| gacggcacca | tgagcgactt | tggtattccg | ccagcatcg | tggcgaaata | cctcgacgaa | 1560 |
| catggcatcg | ttgttgagaa | aaccggtccg | tataacctgc | tgttcctgtt | cagcatcggt | 1620 |

-continued

```
atcgataaga ccaaagcact gagcctgctg cgtgctctga ctgactttaa acgtgcgttc    1680
gacctgaacc tgcgtgtgaa aaacatgctg ccgtctctgt atcgtgaaga tcctgaattc    1740
tatgaaaaca tgcgtattca ggaactggct cagaatatcc acaaactgat tgttcaccac    1800
aatctgccgg atctgatgta tcgcgcattt gaagtgctgc cgacgatggt aatgactccg    1860
tatgctgcat tccagaaaga gctgcacggt atgaccgaag aagtttacct cgacgaaatg    1920
gtaggtcgta ttaacgccaa tatgatcctt ccgtacccgc cgggagttcc tctggtaatg    1980
ccgggtgaaa tgatcaccga agaaagccgt ccggttctgg agttcctgca gatgctgtgt    2040
gaaatcggcg ctcactatcc gggctttgaa accgatattc acggtgcata ccgtcaggct    2100
gatggccgct ataccgttaa ggtattgaaa gaagaaagca aaaataa                  2148
```

<210> SEQ ID NO 2
<211> LENGTH: 715
<212> TYPE: PRT
<213> ORGANISM: Escherichia coli

<400> SEQUENCE: 2

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
```

```
                275                 280                 285
Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
                355                 360                 365

Leu Ala Ala Phe Ser Gln Ala Ser Met Ile His Val Lys Gly Asp Val
370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
                435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
                515                 520                 525

Gly Pro Tyr Asn Leu Leu Phe Leu Phe Ser Ile Gly Ile Asp Lys Thr
530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
                580                 585                 590

Ile His Lys Leu Ile Val His His Asn Leu Pro Asp Leu Met Tyr Arg
                595                 600                 605

Ala Phe Glu Val Leu Pro Thr Met Val Met Thr Pro Tyr Ala Ala Phe
610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
                675                 680                 685

Phe Glu Thr Asp Ile His Gly Ala Tyr Arg Gln Ala Asp Gly Arg Tyr
690                 695                 700
```

Thr Val Lys Val Leu Lys Glu Glu Ser Lys Lys
705               710               715

<210> SEQ ID NO 3
<211> LENGTH: 186
<212> TYPE: DNA
<213> ORGANISM: Escherichia coli

<400> SEQUENCE: 3

| | | |
|---|---|---|
| atgctgattc tgactcgtcg agttggtgag accctcatga ttggggatga ggtcaccgtg | 60 |
| acagttttag gggtaaaggg caaccaggta cgtattggcg taaatgcccc gaaggaagtt | 120 |
| tctgttcacc gtgaagagat ctaccagcgt atccaggctg aaaaatccca gcagtccagt | 180 |
| tactaa | 186 |

<210> SEQ ID NO 4
<211> LENGTH: 61
<212> TYPE: PRT
<213> ORGANISM: Escherichia coli

<400> SEQUENCE: 4

Met Leu Ile Leu Thr Arg Arg Val Gly Glu Thr Leu Met Ile Gly Asp
1               5                   10                  15

Glu Val Thr Val Thr Val Leu Gly Val Lys Gly Asn Gln Val Arg Ile
            20                  25                  30

Gly Val Asn Ala Pro Lys Glu Val Ser Val His Arg Glu Glu Ile Tyr
        35                  40                  45

Gln Arg Ile Gln Ala Glu Lys Ser Gln Gln Ser Ser Tyr
    50                  55                  60

<210> SEQ ID NO 5
<211> LENGTH: 1941
<212> TYPE: DNA
<213> ORGANISM: Escherichia coli

<400> SEQUENCE: 5

| | |
|---|---|
| atgagattaa cgacgaaatt ttcggccttt gttacgctgc tcaccggggtt aacaattttt | 60 |
| gtgactttgc tgggctgttc gctaagtttc tacaacgcca ttcagtataa gtttagtcat | 120 |
| cgcgttcagg cggtggcgac ggcgattgat acccaccttg tgtcgaatga cttcagcgta | 180 |
| ttaaggccac aaattaccga ttaatgatg tcggcagata tcgttcgtgt agacctgctc | 240 |
| catggtgata acaggtttta ccctggcc agaaatggta gttatcgtcc agttggctcc | 300 |
| agcgatctgt ttcgcgaact gagcgttccg ttgataaagc atccggggat gtcgttgcgt | 360 |
| ctggtttatc aggacccgat gggcaactat ttccattcgt tgatgaccac cgcgccgctc | 420 |
| acgggggcga ttggctttat cattgttatg ctcttcctgg cggtacgctg gttacaacgg | 480 |
| caacttgccg gcaagaatt gctggaaacc cgggctactc gtatcttaaa cggtgagcgt | 540 |
| ggctctaatg tgttgggaac catctatgaa tggccgccca gaaccagcag tgcgctggat | 600 |
| acgctgcttc gtgaaattca gaacgcacgc gaacaacaca gccgtcttga tacgctgatc | 660 |
| cgctcttatg ccgcccagga cgtgaaaacc ggcctcaata accgactctt tttcgataat | 720 |
| cagttagcaa cgttactgga agatcaggag aaagtaggta cccacgggat cgtgatgatg | 780 |
| attcgtctgc cggatttcaa tatgttgagc gatacctggg ggcacagcca ggttgaagaa | 840 |
| cagttcttca ctctgacgaa tctgctgtcg acatttatga tgcgctaccc tggcgcactg | 900 |
| ctggcgcgtt accaccgcag tgattttgct gcgctgttac cgcaccggac gttaaaagag | 960 |

-continued

```
gcagagagca tcgccggtca gttaatcaaa gccgttgata ccttgccgaa caataaaatg   1020
ctcgatcgcg acgatatgat ccacattggt atctgcgcct ggcgtagtgg tcaggatacc   1080
gagcaggtaa tggaacatgc agagtctgcc acgcgtaatg cgggattgca gggcggcaat   1140
agctgggcta tttacgatga ctcgttgcct gaaaaaggac gcggtaatgt tcgctggcgt   1200
acgcttatcg agcaaatgct cagtcgcggc ggcccgcgcc tttatcaaaa accggcggtt   1260
actcgcgaag gtcaggttca tcatcgcgaa ctcatgtgcc gcatcttcga tggtaatgaa   1320
gaggttagct cggcggagta tatgccgatg gtcttgcagt ttggcttatc ggaagagtat   1380
gaccgtctgc aaatcagccg tcttattcca ctattgcgtt actggccaga ggaaaatctg   1440
gcgattcagg ttaccgttga gtcgctgatt cgcccgcgtt ttcagcgttg gctgcgcgat   1500
acgttaatgc aatgtgaaaa atcacaacga aaacgcataa ttattgaact tgcagaggcc   1560
gatgtaggtc aacatatcag tcgtttacaa cctgttattc gtttagtgaa tgctttaggg   1620
gtacgggtag ccgtcaacca ggctggtttg acgctggtaa gtaccagttg gatcaaagaa   1680
cttaatgttg agttactcaa gctccatccg gggctggtca gaaacattga aagcgaacg    1740 gagaaccagc tgctggttca aagcctggtg gaagcctgct ccgggaccag cacccaggtt   1800
tacgccaccg gcgtgcgttc gcgaagcgag tggcagaccc tgattcagcg cggtgttaca   1860
ggcgggcaag gggattttttt cgcgtcctca cagccacttg atactaacgt gaaaaaatat   1920
tcacaaagat actcggttta a                                             1941
```

<210> SEQ ID NO 6
<211> LENGTH: 646
<212> TYPE: PRT
<213> ORGANISM: Escherichia coli

<400> SEQUENCE: 6

```
Met Arg Leu Thr Thr Lys Phe Ser Ala Phe Val Thr Leu Thr Gly
1               5                   10                  15

Leu Thr Ile Phe Val Thr Leu Leu Gly Cys Ser Leu Ser Phe Tyr Asn
            20                  25                  30

Ala Ile Gln Tyr Lys Phe Ser His Arg Val Gln Ala Val Ala Thr Ala
        35                  40                  45

Ile Asp Thr His Leu Val Ser Asn Asp Phe Ser Val Leu Arg Pro Gln
    50                  55                  60

Ile Thr Glu Leu Met Met Ser Ala Asp Ile Val Arg Val Asp Leu Leu
65                  70                  75                  80

His Gly Asp Lys Gln Val Tyr Thr Leu Ala Arg Asn Gly Ser Tyr Arg
                85                  90                  95

Pro Val Gly Ser Ser Asp Leu Phe Arg Glu Leu Ser Val Pro Leu Ile
            100                 105                 110

Lys His Pro Gly Met Ser Leu Arg Leu Val Tyr Gln Asp Pro Met Gly
        115                 120                 125

Asn Tyr Phe His Ser Leu Met Thr Thr Ala Pro Leu Thr Gly Ala Ile
    130                 135                 140

Gly Phe Ile Ile Val Met Leu Phe Leu Ala Val Arg Trp Leu Gln Arg
145                 150                 155                 160

Gln Leu Ala Gly Gln Glu Leu Glu Thr Arg Ala Thr Arg Ile Leu
                165                 170                 175

Asn Gly Glu Arg Gly Ser Asn Val Leu Gly Thr Ile Tyr Glu Trp Pro
            180                 185                 190
```

```
Pro Arg Thr Ser Ser Ala Leu Asp Thr Leu Arg Glu Ile Gln Asn
    195                 200                 205

Ala Arg Glu Gln His Ser Arg Leu Asp Thr Leu Ile Arg Ser Tyr Ala
210                 215                 220

Ala Gln Asp Val Lys Thr Gly Leu Asn Asn Arg Leu Phe Phe Asp Asn
225                 230                 235                 240

Gln Leu Ala Thr Leu Glu Asp Gln Glu Lys Val Gly Thr His Gly
            245                 250                 255

Ile Val Met Met Ile Arg Leu Pro Asp Phe Asn Met Leu Ser Asp Thr
                260                 265                 270

Trp Gly His Ser Gln Val Glu Glu Gln Phe Phe Thr Leu Thr Asn Leu
        275                 280                 285

Leu Ser Thr Phe Met Met Arg Tyr Pro Gly Ala Leu Leu Ala Arg Tyr
    290                 295                 300

His Arg Ser Asp Phe Ala Ala Leu Leu Pro His Arg Thr Leu Lys Glu
305                 310                 315                 320

Ala Glu Ser Ile Ala Gly Gln Leu Ile Lys Ala Val Asp Thr Leu Pro
                325                 330                 335

Asn Asn Lys Met Leu Asp Arg Asp Met Ile His Ile Gly Ile Cys
            340                 345                 350

Ala Trp Arg Ser Gly Gln Asp Thr Glu Gln Val Met Glu His Ala Glu
        355                 360                 365

Ser Ala Thr Arg Asn Ala Gly Leu Gln Gly Gly Asn Ser Trp Ala Ile
    370                 375                 380

Tyr Asp Asp Ser Leu Pro Glu Lys Gly Arg Gly Asn Val Arg Trp Arg
385                 390                 395                 400

Thr Leu Ile Glu Gln Met Leu Ser Arg Gly Gly Pro Arg Leu Tyr Gln
                405                 410                 415

Lys Pro Ala Val Thr Arg Glu Gly Gln Val His His Arg Glu Leu Met
            420                 425                 430

Cys Arg Ile Phe Asp Gly Asn Glu Glu Val Ser Ser Ala Glu Tyr Met
        435                 440                 445

Pro Met Val Leu Gln Phe Gly Leu Ser Glu Glu Tyr Asp Arg Leu Gln
    450                 455                 460

Ile Ser Arg Leu Ile Pro Leu Leu Arg Tyr Trp Pro Glu Glu Asn Leu
465                 470                 475                 480

Ala Ile Gln Val Thr Val Glu Ser Leu Ile Arg Pro Arg Phe Gln Arg
                485                 490                 495

Trp Leu Arg Asp Thr Leu Met Gln Cys Glu Lys Ser Arg Lys Arg
            500                 505                 510

Ile Ile Ile Glu Leu Ala Glu Ala Asp Val Gly Gln His Ile Ser Arg
        515                 520                 525

Leu Gln Pro Val Ile Arg Leu Val Asn Ala Leu Gly Val Arg Val Ala
    530                 535                 540

Val Asn Gln Ala Gly Leu Thr Leu Val Ser Thr Ser Trp Ile Lys Glu
545                 550                 555                 560

Leu Asn Val Glu Leu Leu Lys Leu His Pro Gly Leu Val Arg Asn Ile
                565                 570                 575

Glu Lys Arg Thr Glu Asn Gln Leu Leu Val Gln Ser Leu Val Glu Ala
            580                 585                 590

Cys Ser Gly Thr Ser Thr Gln Val Tyr Ala Thr Gly Val Arg Ser Arg
        595                 600                 605

Ser Glu Trp Gln Thr Leu Ile Gln Arg Gly Val Thr Gly Gly Gln Gly
```

610                 615                 620
Asp Phe Phe Ala Ser Ser Gln Pro Leu Asp Thr Asn Val Lys Lys Tyr
625                 630                 635                 640

Ser Gln Arg Tyr Ser Val
                    645

<210> SEQ ID NO 7
<211> LENGTH: 449
<212> TYPE: PRT
<213> ORGANISM: Escherichia coli

<400> SEQUENCE: 7

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
50                  55                  60

Asp Ala Ile Arg Asn Ile Gln Phe Ala Ile Leu Glu Arg Leu Arg Tyr
65                  70                  75                  80

Pro Asn Val Ile Arg Glu Ile Glu Arg Leu Leu Glu Asn Ile Thr
                85                  90                  95

Val Leu Ala Glu Ala Ala Leu Ala Thr Ser Pro Ala Leu Thr Asp
            100                 105                 110

Glu Leu Val Ser His Gly Glu Leu Met Ser Thr Leu Leu Phe Val Glu
            115                 120                 125

Ile Leu Arg Glu Arg Asp Val Gln Ala Gln Trp Phe Asp Val Arg Lys
130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
            195                 200                 205

Ala Glu Ala Leu His Ala Ser Arg Val Asp Ile Trp Thr Asp Val Pro
210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
            275                 280                 285

Val Cys Asn Lys Thr Glu Asn Pro Pro Leu Phe Arg Ala Leu Ala Leu
290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

```
Ile Ser Val Asp Leu Ile Thr Thr Ser Glu Val Ser Val Ala Leu Thr
                340                 345                 350

Leu Asp Thr Thr Gly Ser Thr Ser Thr Gly Asp Thr Leu Leu Thr Gln
            355                 360                 365

Ser Leu Leu Met Glu Leu Ser Ala Leu Cys Arg Val Glu Val Glu Glu
        370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu

<210> SEQ ID NO 8
<211> LENGTH: 292
<212> TYPE: PRT
<213> ORGANISM: Escherichia coli

<400> SEQUENCE: 8

Met Phe Thr Gly Ser Ile Val Ala Ile Val Thr Pro Met Asp Glu Lys
1               5                   10                  15

Gly Asn Val Cys Arg Ala Ser Leu Lys Lys Leu Ile Asp Tyr His Val
                20                  25                  30

Ala Ser Gly Thr Ser Ala Ile Val Ser Val Gly Thr Thr Gly Glu Ser
            35                  40                  45

Ala Thr Leu Asn His Asp Glu His Ala Asp Val Val Met Met Thr Leu
        50                  55                  60

Asp Leu Ala Asp Gly Arg Ile Pro Val Ile Ala Gly Thr Gly Ala Asn
65                  70                  75                  80

Ala Thr Ala Glu Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Ala Asn
        195                 200                 205

Val Ala Ala Arg Asp Met Ala Gln Met Cys Lys Leu Ala Ala Glu Gly
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255
```

```
Lys Glu Leu Gly Leu Val Ala Thr Asp Thr Leu Arg Leu Pro Met Thr
                260                 265                 270

Pro Ile Thr Asp Ser Gly Arg Glu Thr Val Arg Ala Ala Leu Lys His
            275                 280                 285

Ala Gly Leu Leu
        290

<210> SEQ ID NO 9
<211> LENGTH: 420
<212> TYPE: PRT
<213> ORGANISM: Escherichia coli

<400> SEQUENCE: 9

Met Pro His Ser Leu Phe Ser Thr Asp Thr Asp Leu Thr Ala Glu Asn
1               5                   10                  15

Leu Leu Arg Leu Pro Ala Glu Phe Gly Cys Pro Val Trp Val Tyr Asp
            20                  25                  30

Ala Gln Ile Ile Arg Arg Gln Ile Ala Ala Leu Lys Gln Phe Asp Val
        35                  40                  45

Val Arg Phe Ala Gln Lys Ala Cys Ser Asn Ile His Ile Leu Arg Leu
    50                  55                  60

Met Arg Glu Gln Gly Val Lys Val Asp Ser Val Ser Leu Gly Glu Ile
65                  70                  75                  80

Glu Arg Ala Leu Ala Ala Gly Tyr Asn Pro Gln Thr His Pro Asp Asp
                85                  90                  95

Ile Val Phe Thr Ala Asp Val Ile Asp Gln Ala Thr Leu Glu Arg Val
            100                 105                 110

Ser Glu Leu Gln Ile Pro Val Asn Ala Gly Ser Val Asp Met Leu Asp
        115                 120                 125

Gln Leu Gly Gln Val Ser Pro Gly His Arg Val Trp Leu Arg Val Asn
    130                 135                 140

Pro Gly Phe Gly His Gly His Ser Gln Lys Thr Asn Thr Gly Gly Glu
145                 150                 155                 160

Asn Ser Lys His Gly Ile Trp Tyr Thr Asp Leu Pro Ala Ala Leu Asp
                165                 170                 175

Val Ile Gln Arg His His Leu Gln Leu Val Gly Ile His Met His Ile
            180                 185                 190

Gly Ser Gly Val Asp Tyr Ala His Leu Glu Gln Val Cys Gly Ala Met
        195                 200                 205

Val Arg Gln Val Ile Glu Phe Gly Gln Asp Leu Gln Ala Ile Ser Ala
    210                 215                 220

Gly Gly Gly Leu Ser Val Pro Tyr Gln Gln Gly Glu Glu Ala Val Asp
225                 230                 235                 240

Thr Glu His Tyr Tyr Gly Leu Trp Asn Ala Ala Arg Glu Gln Ile Ala
                245                 250                 255

Arg His Leu Gly His Pro Val Lys Leu Glu Ile Glu Pro Gly Arg Phe
            260                 265                 270

Leu Val Ala Gln Ser Gly Val Leu Ile Thr Gln Val Arg Ser Val Lys
        275                 280                 285

Gln Met Gly Ser Arg His Phe Val Leu Val Asp Ala Gly Phe Asn Asp
    290                 295                 300

Leu Met Arg Pro Ala Met Tyr Gly Ser Tyr His His Ile Ser Ala Leu
305                 310                 315                 320

Ala Ala Asp Gly Arg Ser Leu Glu His Ala Pro Thr Val Glu Thr Val
                325                 330                 335
```

```
Val Ala Gly Pro Leu Cys Glu Ser Gly Asp Val Phe Thr Gln Gln Glu
            340                 345                 350

Gly Gly Asn Val Glu Thr Arg Ala Leu Pro Glu Val Lys Ala Gly Asp
            355                 360                 365

Tyr Leu Val Leu His Asp Thr Gly Ala Tyr Gly Ala Ser Met Ser Ser
    370                 375                 380

Asn Tyr Asn Ser Arg Pro Leu Leu Pro Glu Val Leu Phe Asp Asn Gly
385                 390                 395                 400

Gln Ala Arg Leu Ile Arg Arg Gln Thr Ile Glu Leu Leu Ala
                405                 410                 415

Leu Glu Leu Leu
            420

<210> SEQ ID NO 10
<211> LENGTH: 449
<212> TYPE: PRT
<213> ORGANISM: Artificial Sequence
<220> FEATURE:
<223> OTHER INFORMATION: LysC-1 M318I, G323D  polypeptide sequence

<400> SEQUENCE: 10

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270
```

```
Pro Val Phe Val Gly Ser Ser Lys Asp Pro Arg Ala Gly Gly Thr Leu
            275                 280                 285

Val Cys Asn Lys Thr Glu Asn Pro Pro Leu Phe Arg Ala Leu Ala Leu
            290                 295                 300

Arg Arg Asn Gln Thr Leu Leu Thr Leu His Ser Leu Asn Ile Leu His
305                 310                 315                 320

Ser Arg Asp Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
            355                 360                 365

Ser Leu Leu Met Glu Leu Ser Ala Leu Cys Arg Val Glu Val Glu Glu
            370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
                420                 425                 430

Gly Glu Asp Ala Glu Gln Val Val Gln Lys Leu His Ser Asn Leu Phe
            435                 440                 445

Glu

<210> SEQ ID NO 11
<211> LENGTH: 425
<212> TYPE: PRT
<213> ORGANISM: Artificial Sequence
<220> FEATURE:
<223> OTHER INFORMATION: S-LysC polypeptide sequence

<400> SEQUENCE: 11

Met Gly Leu Val Val Gln Lys Tyr Gly Gly Ser Ser Val Ala Asp Ala
1               5                   10                  15

Glu Gly Ile Lys Arg Val Ala Lys Arg Ile Val Glu Ala Lys Lys Asn
            20                  25                  30

Gly Asn Gln Val Val Ala Val Val Ser Ala Met Gly Asp Thr Thr Asp
            35                  40                  45

Glu Leu Ile Asp Leu Ala Glu Gln Val Ser Pro Ile Pro Ala Gly Arg
        50                  55                  60

Glu Leu Asp Met Leu Leu Thr Ala Gly Glu Arg Ile Ser Met Ala Leu
65                  70                  75                  80

Leu Ala Met Ala Ile Lys Asn Leu Gly His Glu Ala Gln Ser Phe Thr
                85                  90                  95

Gly Ser Gln Ala Gly Val Ile Thr Asp Ser Val His Asn Lys Ala Arg
            100                 105                 110

Ile Ile Asp Val Thr Pro Gly Arg Ile Arg Thr Ser Val Asp Glu Gly
            115                 120                 125

Asn Val Ala Ile Val Ala Gly Phe Gln Gly Val Ser Gln Asp Ser Lys
        130                 135                 140

Asp Ile Thr Thr Leu Gly Arg Gly Gly Ser Asp Thr Thr Ala Val Ala
145                 150                 155                 160

Leu Ala Ala Ala Leu Asp Ala Asp Val Cys Glu Ile Tyr Thr Asp Val
                165                 170                 175
```

```
Asp Gly Val Phe Thr Ala Asp Pro Arg Val Val Pro Lys Ala Lys Lys
            180                 185                 190

Ile Asp Trp Ile Ser Phe Glu Asp Met Leu Glu Leu Ala Ala Ser Gly
        195                 200                 205

Ser Lys Val Leu Leu His Arg Cys Val Glu Tyr Ala Arg Arg Tyr Asn
    210                 215                 220

Ile Pro Ile His Val Arg Ser Ser Phe Ser Gly Leu Gln Gly Thr Trp
225                 230                 235                 240

Val Ser Ser Glu Pro Ile Lys Gln Gly Lys His Val Glu Gln Ala
            245                 250                 255

Leu Ile Ser Gly Val Ala His Asp Thr Ser Glu Ala Lys Val Thr Val
            260                 265                 270

Val Gly Val Pro Asp Lys Pro Gly Glu Ala Ala Ile Phe Arg Ala
            275                 280                 285

Ile Ala Asp Ala Gln Val Asn Ile Asp Met Val Val Gln Asn Val Ser
290                 295                 300

Ala Ala Ser Thr Gly Leu Thr Asp Ile Ser Phe Thr Leu Pro Lys Ser
305                 310                 315                 320

Glu Gly Arg Lys Ala Ile Asp Ala Leu Glu Lys Asn Arg Pro Gly Ile
            325                 330                 335

Gly Phe Asp Ser Leu Arg Tyr Asp Asp Gln Ile Gly Lys Ile Ser Leu
            340                 345                 350

Val Gly Ala Gly Met Lys Ser Asn Pro Gly Val Thr Ala Asp Phe Phe
            355                 360                 365

Thr Ala Leu Ser Asp Ala Gly Val Asn Ile Glu Leu Ile Ser Thr Ser
370                 375                 380

Glu Ile Arg Ile Ser Val Val Thr Arg Lys Asp Asp Val Asn Glu Ala
385                 390                 395                 400

Val Arg Ala Val His Thr Ala Phe Gly Leu Asp Ser Asp Ser Asp Glu
            405                 410                 415

Ala Val Val Tyr Gly Gly Thr Gly Arg
            420                 425

<210> SEQ ID NO 12
<211> LENGTH: 350
<212> TYPE: PRT
<213> ORGANISM: Escherichia coli

<400> SEQUENCE: 12

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
            85                  90                  95

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
        115                 120                 125
```

Thr Phe Val Gly Gly Asn Cys Thr Val Ser Leu Met Leu Met Ser Leu
                130                 135                 140

Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
                165                 170                 175

Thr Gln Met Gly His Leu Tyr Gly His Val Ala Asp Glu Leu Ala Thr
                180                 185                 190

Pro Ser Ser Ala Ile Leu Asp Ile Glu Arg Lys Val Thr Thr Leu Thr
                195                 200                 205

Arg Ser Gly Glu Leu Pro Val Asp Asn Phe Gly Val Pro Leu Ala Gly
210                 215                 220

Ser Leu Ile Pro Trp Ile Asp Lys Gln Leu Asp Asn Gly Gln Ser Arg
225                 230                 235                 240

Glu Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
                260                 265                 270

Cys His Ser Gln Ala Phe Thr Ile Lys Leu Lys Asp Val Ser Ile
                275                 280                 285

Pro Thr Val Glu Glu Leu Leu Ala Ala His Asn Pro Trp Ala Lys Val
                290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln
                340                 345                 350

<210> SEQ ID NO 13
<211> LENGTH: 273
<212> TYPE: PRT
<213> ORGANISM: Escherichia coli

<400> SEQUENCE: 13

Met His Asp Ala Asn Ile Arg Val Ala Ile Ala Gly Ala Gly Gly Arg
1               5                   10                  15

Met Gly Arg Gln Leu Ile Gln Ala Ala Leu Ala Leu Glu Gly Val Gln
                20                  25                  30

Leu Gly Ala Ala Leu Glu Arg Glu Gly Ser Ser Leu Leu Gly Ser Asp
                35                  40                  45

Ala Gly Glu Leu Ala Gly Ala Gly Lys Thr Gly Val Thr Val Gln Ser
                50                  55                  60

Ser Leu Asp Ala Val Lys Asp Phe Asp Val Phe Ile Asp Phe Thr
65                  70                  75                  80

Arg Pro Glu Gly Thr Leu Asn His Leu Ala Phe Cys Arg Gln His Gly
                85                  90                  95

Lys Gly Met Val Ile Gly Thr Thr Gly Phe Asp Glu Ala Gly Lys Gln
                100                 105                 110

Ala Ile Arg Asp Ala Ala Asp Ile Ala Ile Val Phe Ala Ala Asn
                115                 120                 125

Phe Ser Val Gly Val Asn Val Met Leu Lys Leu Leu Glu Lys Ala Ala
130                 135                 140

Lys Val Met Gly Asp Tyr Thr Asp Ile Glu Ile Ile Glu Ala His His

```
                     145                 150                 155                 160
Arg His Lys Val Asp Ala Pro Ser Gly Thr Ala Leu Ala Met Gly Glu
                165                 170                 175

Ala Ile Ala His Ala Leu Asp Lys Asp Leu Lys Asp Cys Ala Val Tyr
            180                 185                 190

Ser Arg Glu Gly His Thr Gly Glu Arg Val Pro Gly Thr Ile Gly Phe
        195                 200                 205

Ala Thr Val Arg Ala Gly Asp Ile Val Gly Glu His Thr Ala Met Phe
    210                 215                 220

Ala Asp Ile Gly Glu Arg Leu Glu Ile Thr His Lys Ala Ser Ser Arg
225                 230                 235                 240

Met Thr Phe Ala Asn Gly Ala Val Arg Ser Ala Leu Trp Leu Ser Gly
                245                 250                 255

Lys Glu Ser Gly Leu Phe Asp Met Arg Asp Val Leu Asp Leu Asn Asn
            260                 265                 270

Leu

<210> SEQ ID NO 14
<211> LENGTH: 274
<212> TYPE: PRT
<213> ORGANISM: Escherichia coli

<400> SEQUENCE: 14

Met Gln Gln Leu Gln Asn Ile Ile Glu Thr Ala Phe Glu Arg Arg Ala
1               5                   10                  15

Glu Ile Thr Pro Ala Asn Ala Asp Thr Val Thr Arg Glu Ala Val Asn
            20                  25                  30

Gln Val Ile Ala Leu Leu Asp Ser Gly Ala Leu Arg Val Ala Glu Lys
        35                  40                  45

Ile Asp Gly Gln Trp Val Thr His Gln Trp Leu Lys Lys Ala Val Leu
    50                  55                  60

Leu Ser Phe Arg Ile Asn Asp Asn Gln Val Ile Glu Gly Ala Glu Ser
65                  70                  75                  80

Arg Tyr Phe Asp Lys Val Pro Met Lys Phe Ala Asp Tyr Asp Glu Ala
                85                  90                  95

Arg Phe Gln Lys Glu Gly Phe Arg Val Val Pro Pro Ala Ala Val Arg
            100                 105                 110

Gln Gly Ala Phe Ile Ala Arg Asn Thr Val Leu Met Pro Ser Tyr Val
        115                 120                 125

Asn Ile Gly Ala Tyr Val Asp Glu Gly Thr Met Val Asp Thr Trp Ala
    130                 135                 140

Thr Val Gly Ser Cys Ala Gln Ile Gly Lys Asn Val His Leu Ser Gly
145                 150                 155                 160

Gly Val Gly Ile Gly Gly Val Leu Glu Pro Leu Gln Ala Asn Pro Thr
                165                 170                 175

Ile Ile Glu Asp Asn Cys Phe Ile Gly Ala Arg Ser Glu Val Val Glu
            180                 185                 190

Gly Val Ile Val Glu Glu Gly Ser Val Ile Ser Met Gly Val Tyr Ile
        195                 200                 205

Gly Gln Ser Thr Arg Ile Tyr Asp Arg Glu Thr Gly Glu Ile His Tyr
    210                 215                 220

Gly Arg Val Pro Ala Gly Ser Val Val Ser Gly Asn Leu Pro Ser
225                 230                 235                 240

Lys Asp Gly Lys Tyr Ser Leu Tyr Cys Ala Val Ile Val Lys Lys Val
```

```
                        245                 250                 255
Asp Ala Lys Thr Arg Gly Lys Val Gly Ile Asn Glu Leu Leu Arg Thr
                    260                 265                 270
Ile Asp

<210> SEQ ID NO 15
<211> LENGTH: 396
<212> TYPE: PRT
<213> ORGANISM: Escherichia coli

<400> SEQUENCE: 15

Met Phe Glu Asn Ile Thr Ala Ala Pro Ala Asp Pro Ile Leu Gly Leu
1               5                   10                  15

Ala Asp Leu Phe Arg Ala Asp Glu Arg Pro Gly Lys Ile Asn Leu Gly
            20                  25                  30

Ile Gly Val Tyr Lys Asp Glu Thr Gly Lys Thr Pro Val Leu Thr Ser
        35                  40                  45

Val Lys Lys Ala Glu Gln Tyr Leu Leu Glu Asn Glu Thr Thr Lys Asn
    50                  55                  60

Tyr Leu Gly Ile Asp Gly Ile Pro Glu Phe Gly Arg Cys Thr Gln Glu
65                  70                  75                  80

Leu Leu Phe Gly Lys Gly Ser Ala Leu Ile Asn Asp Lys Arg Ala Arg
                85                  90                  95

Thr Ala Gln Thr Pro Gly Gly Thr Gly Ala Leu Arg Val Ala Ala Asp
            100                 105                 110

Phe Leu Ala Lys Asn Thr Ser Val Lys Arg Val Trp Val Ser Asn Pro
        115                 120                 125

Ser Trp Pro Asn His Lys Ser Val Phe Asn Ser Ala Gly Leu Glu Val
    130                 135                 140

Arg Glu Tyr Ala Tyr Tyr Asp Ala Glu Asn His Thr Leu Asp Phe Asp
145                 150                 155                 160

Ala Leu Ile Asn Ser Leu Asn Glu Ala Gln Ala Gly Asp Val Val Leu
                165                 170                 175

Phe His Gly Cys Cys His Asn Pro Thr Gly Ile Asp Pro Thr Leu Glu
            180                 185                 190

Gln Trp Gln Thr Leu Ala Gln Leu Ser Val Glu Lys Gly Trp Leu Pro
        195                 200                 205

Leu Phe Asp Phe Ala Tyr Gln Gly Phe Ala Arg Gly Leu Glu Glu Asp
    210                 215                 220

Ala Glu Gly Leu Arg Ala Phe Ala Ala Met His Lys Glu Leu Ile Val
225                 230                 235                 240

Ala Ser Ser Tyr Ser Lys Asn Phe Gly Leu Tyr Asn Glu Arg Val Gly
                245                 250                 255

Ala Cys Thr Leu Val Ala Ala Asp Ser Glu Thr Val Asp Arg Ala Phe
            260                 265                 270

Ser Gln Met Lys Ala Ala Ile Arg Ala Asn Tyr Ser Asn Pro Pro Ala
        275                 280                 285

His Gly Ala Ser Val Val Ala Thr Ile Leu Ser Asn Asp Ala Leu Arg
    290                 295                 300

Ala Ile Trp Glu Gln Glu Leu Thr Asp Met Arg Gln Arg Ile Gln Arg
305                 310                 315                 320

Met Arg Gln Leu Phe Val Asn Thr Leu Gln Glu Lys Gly Ala Asn Arg
                325                 330                 335

Asp Phe Ser Phe Ile Ile Lys Gln Asn Gly Met Phe Ser Phe Ser Gly
```

```
                340                 345                 350
Leu Thr Lys Glu Gln Val Leu Arg Leu Arg Glu Glu Phe Gly Val Tyr
            355                 360                 365

Ala Val Ala Ser Gly Arg Val Asn Val Ala Gly Met Thr Pro Asp Asn
        370                 375                 380

Met Ala Pro Leu Cys Glu Ala Ile Val Ala Val Leu
385                 390                 395

<210> SEQ ID NO 16
<211> LENGTH: 360
<212> TYPE: DNA
<213> ORGANISM: Escherichia coli

<400> SEQUENCE: 16
gagtcagaca acgaagtgaa catcaggatg atgacacttc tgcaggacac accaggatgg    60
tgtttcaggg aaaggcttct ggatgaagcg aagaggatga cgcaggacgc gttaaaggac   120
acctccagga tggagaatga aaccggtca ggatgattcg gtgggtcagg aaggccaggg    180
acacttcagg atgaagtatc acatcggggt ggtgtgagca ggaagcaata gttcaggatg   240
aacgattggc cgcaaggcca gaggaaaagt tgtcaaggat gagcagggag caacaaaagt   300
agctggaatg ctgcgaaacg aaccgggagc gctgtgaata cagtgctccc ttttttatt    360

<210> SEQ ID NO 17
<211> LENGTH: 245
<212> TYPE: DNA
<213> ORGANISM: Escherichia coli

<400> SEQUENCE: 17
atagagcgag gacgctaaca ggaacaatga ctcaggatga gggtcaggag cgccaggagg    60
cgaagacaga ggattgtcag gaagacaaac gtccggagac gtaattaaac ggaaatggaa   120
tcaacacgga ttgttccggc taaaggaaaa acagggtgtg ttggcggcct gcaaggattg   180
taagacccgt taagggttat gagtcaggaa aaaaggcgac agagtaatct gtcgcctttt   240
ttctt                                                               245

<210> SEQ ID NO 18
<211> LENGTH: 360
<212> TYPE: DNA
<213> ORGANISM: Shigella flexneri

<400> SEQUENCE: 18
gagtcagaca acgaagtgaa catcaggatg atgacacttc tgcaggacac accaggatgg    60
tgtttcaggg aaaggcttct ggatgaagcg aagaggatga cgcaggacgc gttaaaggac   120
acctccagga tggagaatga aaccggtca ggatgattcg gtgggtcagg aaggccaggg    180
acacttcagg atgaagtatc acatcggggt ggtgtgagca ggaagcaata gttcaggatg   240
aacgattggc cgcaaggcca gaggaaaagt tgtcaaggat gagcagggag caacaaaagt   300
agctggaatg ctgcgaaacg aaccgggagc actgtgaata cagtgctccc ttttttatt    360

<210> SEQ ID NO 19
<211> LENGTH: 360
<212> TYPE: DNA
<213> ORGANISM: Triticum aestivum

<400> SEQUENCE: 19
gagtcagaca acgaagtgaa catcaggatg atgacacttc tgcaggaaac accaggatgg    60
```

```
tgtttcaggg aaaggcttct ggatgaagcg aagaggatga cgcaggacgc gttaaaggac    120
acctccagga tggagaatga gaaccggtca ggatgattcg gtgggtcagg aaggccaggg    180
acacttcagg atgaagtatc acatcggggt ggtgtgagca ggaagcaata gttcaggatg    240
aacgattggc cgcaaggcca gaggaaaagt tgtcaaggat gagcagggag caacaaaagt    300
agctggaatg ctgcgaaacg aaccgggagc gctgtgaata cagtgctccc ttttttatt     360

<210> SEQ ID NO 20
<211> LENGTH: 360
<212> TYPE: DNA
<213> ORGANISM: Shigella sonnei

<400> SEQUENCE: 20
gagtcagaca acgaagtgaa catcaggatg atgacacttc tgcaggacac accaggatgg     60
tgtttcaggg aaaggcttct ggatgaagcg aagaggatga cgcaggacgc gttaaaggac    120
acctccagga tggagaatga gaaccggtca ggatgattcg gtgggtcagg aaggccaggg    180
acacttcagg atgaagtatc acatcggggt ggtgtgagca ggaagcaata gttcaggatg    240
aacgattggc cgcaaggcca gaggaaaagt tgtcaaggat gagcagggag caacaaaagt    300
agctggaatg ctgcgaaacg aaccgggagc actgtgaata cagtgctccc ttttttatt     360

<210> SEQ ID NO 21
<211> LENGTH: 358
<212> TYPE: DNA
<213> ORGANISM: Citrobacter sp.

<400> SEQUENCE: 21
gagtcgcaca acgaagtgaa catcaggatg atgacacttc agcaggacac accaggacgg     60
tgttacaggg aaaggcttca ggatgaagtg aagaggataa cgcgggaatg cgttaaagga    120
cacctccagg aaggagaacg agagccggtc aggatagtcg gtgggtcagg atggccagga    180
tgcttcagga tgaagtaatc acatcggggt ggtgtgagca ggatgcaaaa tgttcaggat    240
gaacaacagg tcgcaagacc agaggaaaag ttgtcacgga tgagcaggga gcacaaaaag    300
tagctggaat gctgcgaaac gaaccgggag cactgttttt acagtgctcc ctttttt      358

<210> SEQ ID NO 22
<211> LENGTH: 353
<212> TYPE: DNA
<213> ORGANISM: Salmonella enterica

<400> SEQUENCE: 22
gagtcgtaca acgaagcgaa cgtcaggatg atgacgcttc agcaggacac gccaggatgg     60
tgttacaagg aaaggcttca ggatgaagca aagtggaaag cgcaggatgc gttaaaggac    120
acctccagga cggagaacga gagccgatca ggatgttcgg cgggtctgga tgaccaggga    180
cgcttcagga tgaagctatc acatcggcg atgtgcgcag gatgcaaacg ttcaggatga    240
acaggccgta aggtcacagg aaaagttgtc acgatgagc agggagcacg aaaagtagct    300
ggaatgctgc gaaacgaacc gggagcactg tttatacagt gctccctttt ttt          353

<210> SEQ ID NO 23
<211> LENGTH: 245
<212> TYPE: DNA
<213> ORGANISM: Shigella sonnei

<400> SEQUENCE: 23
atagagcgag gacgctaaca ggaacaatga ctcaggatga gggtcaggag cgccaggagg     60
```

```
cgaagacaga ggattgtcag gaagacaaac gtccggagac gtaattaaac ggaaatggaa      120
tcaacacgga ttgttccggc taaaggaaaa acagggtgtg ttggcggcct gcaaggattg      180
taagacccgt taagggttat gagtcaggaa aaaaggcgac agagtaatct gtcgcctttt      240
ttctt                                                                  245

<210> SEQ ID NO 24
<211> LENGTH: 245
<212> TYPE: DNA
<213> ORGANISM: Shigella flexneri

<400> SEQUENCE: 24
atagagcgag gacgctaaca ggaacaatga ctcaggatga gggtcaggag cgccaggagg       60
cgaagacaga ggattgtcag gaagacaaac gtccggagac gtaattaaac ggaaatggaa      120
tcaacacgga ttgttccggc taatggaaaa acagggtgtg ttggcggcct gcaaggattg      180
taagacccgt taagggttat gagtcaggaa aaaaggcgac agagtaatct gtcgcctttt      240
ttctt                                                                  245

<210> SEQ ID NO 25
<211> LENGTH: 242
<212> TYPE: DNA
<213> ORGANISM: Citrobacter werkmaniii

<400> SEQUENCE: 25
agcgagggag ctaacaggat aaacgactca ggatgagggt caggagcgcc aggaggcgaa       60
gacgcaggat tgtcaggaag acaaacgtcc ggagacgtta gtaaaggaa atggaaacaa      120 cacggaatgt ttctggctaa gggaaaaaca gggtgtgttg atagccgaca gggattgtag      180
ggcccgttaa gggttgagag tcaggaaaaa aggcgacaga ttactctgtc gccttttttc      240
tt                                                                     242

<210> SEQ ID NO 26
<211> LENGTH: 242
<212> TYPE: DNA
<213> ORGANISM: Salmonella enterica

<400> SEQUENCE: 26
agcgaggacg ctaacaggat caacgactca ggatgagggt caggagcgcc aggaggcgaa       60
gacacaggat tgtcaggaag acaaacgtcc ggagacgtta gtaaaggaa atggaaacaa      120 catggaatgt tccaggctaa gggaaaaaca gggcgtgttg atagccaaca gggatggtgg      180
aacccgttaa gggtcgtgag tcaagaaaaa aggcggcaga ttactctgtc gccttttttc      240
tt                                                                     242

<210> SEQ ID NO 27
<211> LENGTH: 50
<212> TYPE: DNA
<213> ORGANISM: Artificial Sequence
<220> FEATURE:
<223> OTHER INFORMATION: Primer cadA-F

<400> SEQUENCE: 27
ggcgagctca cacaggaaac agaccatgaa cgttattgca atattgaatc                  50

<210> SEQ ID NO 28
<211> LENGTH: 53
<212> TYPE: DNA
```

```
<213> ORGANISM: Artificial Sequence
<220> FEATURE:
<223> OTHER INFORMATION: Primer cadA-R

<400> SEQUENCE: 28
ggcggatccc cacttccctt gtacgagcta attatttttt gctttcttct ttc          53

<210> SEQ ID NO 29
<211> LENGTH: 47
<212> TYPE: DNA
<213> ORGANISM: Artificial Sequence
<220> FEATURE:
<223> OTHER INFORMATION: Primer cadA-F2

<400> SEQUENCE: 29
atttcacaca ggaaacagct atgaacgtta ttgcaatatt gaatcac                 47

<210> SEQ ID NO 30
<211> LENGTH: 20
<212> TYPE: DNA
<213> ORGANISM: Artificial Sequence
<220> FEATURE:
<223> OTHER INFORMATION: Primer cadA-R2

<400> SEQUENCE: 30
agctgtttcc tgtgtgaaat                                               20

<210> SEQ ID NO 31
<211> LENGTH: 35
<212> TYPE: DNA
<213> ORGANISM: Artificial Sequence
<220> FEATURE:
<223> OTHER INFORMATION: Primer SacI-F

<400> SEQUENCE: 31
ggcgagctcc tcctgtgtga aattgttatc cgctc                              35

<210> SEQ ID NO 32
<211> LENGTH: 34
<212> TYPE: DNA
<213> ORGANISM: Artificial Sequence
<220> FEATURE:
<223> OTHER INFORMATION: Primer SacI-R

<400> SEQUENCE: 32
ggcgagctca tgaacgttat tgcaatattg aatc                               34

<210> SEQ ID NO 33
<211> LENGTH: 29
<212> TYPE: DNA
<213> ORGANISM: Artificial Sequence
<220> FEATURE:
<223> OTHER INFORMATION: Primer csrA-F

<400> SEQUENCE: 33
ggcgagctca tgctgattct gactcgtcg                                     29

<210> SEQ ID NO 34
<211> LENGTH: 31
<212> TYPE: DNA
<213> ORGANISM: Artificial Sequence
<220> FEATURE:
<223> OTHER INFORMATION: Primer csrA-R

<400> SEQUENCE: 34
ggcggatcct tagtaactgg actgctggga t                                  31
```

<210> SEQ ID NO 35
<211> LENGTH: 33
<212> TYPE: DNA
<213> ORGANISM: Artificial Sequence
<220> FEATURE:
<223> OTHER INFORMATION: Primer csrD-F

<400> SEQUENCE: 35
ggcgagctca tgagattaac gacgaaattt tcg        33

<210> SEQ ID NO 36
<211> LENGTH: 34
<212> TYPE: DNA
<213> ORGANISM: Artificial Sequence
<220> FEATURE:
<223> OTHER INFORMATION: Primer csrD-R

<400> SEQUENCE: 36
ggcggatcct taaaccgagt atctttgtga atat        34

<210> SEQ ID NO 37
<211> LENGTH: 22
<212> TYPE: DNA
<213> ORGANISM: Artificial Sequence
<220> FEATURE:
<223> OTHER INFORMATION: Primer rmvBamHI-F

<400> SEQUENCE: 37
gtttatcagg acccgatggg ca        22

<210> SEQ ID NO 38
<211> LENGTH: 22
<212> TYPE: DNA
<213> ORGANISM: Artificial Sequence
<220> FEATURE:
<223> OTHER INFORMATION: Primer rmvBamHI-R

<400> SEQUENCE: 38
tgcccatcgg gtcctgataa ac        22

<210> SEQ ID NO 39
<211> LENGTH: 46
<212> TYPE: DNA
<213> ORGANISM: Artificial Sequence
<220> FEATURE:
<223> OTHER INFORMATION: Primer lysC-F

<400> SEQUENCE: 39
ggcgagctca cacaggaaac agaccatgtc tgaaattgtt gtctcc        46

<210> SEQ ID NO 40
<211> LENGTH: 33
<212> TYPE: DNA
<213> ORGANISM: Artificial Sequence
<220> FEATURE:
<223> OTHER INFORMATION: Primer lysC-R

<400> SEQUENCE: 40
ggcggatcct tactcaaaca aattactatg cag        33

<210> SEQ ID NO 41
<211> LENGTH: 46
<212> TYPE: DNA
<213> ORGANISM: Artificial Sequence
<220> FEATURE:

<223> OTHER INFORMATION: Primer dapA-F

<400> SEQUENCE: 41
ggcggatcca cacaggaaac agaccatgtt cacgggaagt attgtc          46

<210> SEQ ID NO 42
<211> LENGTH: 28
<212> TYPE: DNA
<213> ORGANISM: Artificial Sequence
<220> FEATURE:
<223> OTHER INFORMATION: Primer dapA-R

<400> SEQUENCE: 42
ggctctagat tacagcaaac cggcatgc          28

<210> SEQ ID NO 43
<211> LENGTH: 46
<212> TYPE: DNA
<213> ORGANISM: Artificial Sequence
<220> FEATURE:
<223> OTHER INFORMATION: Primer lysA-F

<400> SEQUENCE: 43
ggctctagaa cacaggaaac agaccatgcc acattcactg ttcagc          46

<210> SEQ ID NO 44
<211> LENGTH: 30
<212> TYPE: DNA
<213> ORGANISM: Artificial Sequence
<220> FEATURE:
<223> OTHER INFORMATION: Primer lysA-R

<400> SEQUENCE: 44
ggcgtcgact taaagcaatt ccagcgccag          30

<210> SEQ ID NO 45
<211> LENGTH: 23
<212> TYPE: DNA
<213> ORGANISM: Artificial Sequence
<220> FEATURE:
<223> OTHER INFORMATION: Primer 318-F

<400> SEQUENCE: 45
cagcctgaat atactgcatt ctc          23

<210> SEQ ID NO 46
<211> LENGTH: 23
<212> TYPE: DNA
<213> ORGANISM: Artificial Sequence
<220> FEATURE:
<223> OTHER INFORMATION: Primer 318-R

<400> SEQUENCE: 46
gagaatgcag tatattcagg ctg          23

<210> SEQ ID NO 47
<211> LENGTH: 20
<212> TYPE: DNA
<213> ORGANISM: Artificial Sequence
<220> FEATURE:
<223> OTHER INFORMATION: Primer 323-F

<400> SEQUENCE: 47
gcattctcgc gatttcctcg          20

```
<210> SEQ ID NO 48
<211> LENGTH: 20
<212> TYPE: DNA
<213> ORGANISM: Artificial Sequence
<220> FEATURE:
<223> OTHER INFORMATION: Primer 323-R

<400> SEQUENCE: 48
cgaggaaatc gcgagaatgc                                               20

<210> SEQ ID NO 49
<211> LENGTH: 46
<212> TYPE: DNA
<213> ORGANISM: Artificial Sequence
<220> FEATURE:
<223> OTHER INFORMATION: Primer SlysC-F

<400> SEQUENCE: 49
ggcgagctca cacaggaaac agaccatggg cttagttgtg cagaaa                  46

<210> SEQ ID NO 50
<211> LENGTH: 30
<212> TYPE: DNA
<213> ORGANISM: Artificial Sequence
<220> FEATURE:
<223> OTHER INFORMATION: Primer SlysC-R

<400> SEQUENCE: 50
ggcggatcct taacgacctg tgccgccata                                    30

<210> SEQ ID NO 51
<211> LENGTH: 48
<212> TYPE: DNA
<213> ORGANISM: Artificial Sequence
<220> FEATURE:
<223> OTHER INFORMATION: Primer asd-F

<400> SEQUENCE: 51
ggcgagctca cacaggaaac agaccatgaa aaatgttggt tttatcgg                48

<210> SEQ ID NO 52
<211> LENGTH: 28
<212> TYPE: DNA
<213> ORGANISM: Artificial Sequence
<220> FEATURE:
<223> OTHER INFORMATION: Primer asd-R

<400> SEQUENCE: 52
ggcggatcct tacgccagtt gacgaagc                                      28

<210> SEQ ID NO 53
<211> LENGTH: 39
<212> TYPE: DNA
<213> ORGANISM: Artificial Sequence
<220> FEATURE:
<223> OTHER INFORMATION: Primer dapB-F

<400> SEQUENCE: 53
ggcacacagg aaacagacca tgcatgatgc aaacatccg                          39

<210> SEQ ID NO 54
<211> LENGTH: 38
<212> TYPE: DNA
<213> ORGANISM: Artificial Sequence
<220> FEATURE:
<223> OTHER INFORMATION: Primer dapB-R
```

<400> SEQUENCE: 54
ggctctagat tacaaattat tgagatcaag tacatctc        38

<210> SEQ ID NO 55
<211> LENGTH: 45
<212> TYPE: DNA
<213> ORGANISM: Artificial Sequence
<220> FEATURE:
<223> OTHER INFORMATION: Primer dapD-F

<400> SEQUENCE: 55
ggctctagaa cacaggaaac agaccatgca gcagttacag aacat        45

<210> SEQ ID NO 56
<211> LENGTH: 29
<212> TYPE: DNA
<213> ORGANISM: Artificial Sequence
<220> FEATURE:
<223> OTHER INFORMATION: Primer dapD-R

<400> SEQUENCE: 56
ggcgcatgct tagtcgatgg tacgcagca        29

<210> SEQ ID NO 57
<211> LENGTH: 46
<212> TYPE: DNA
<213> ORGANISM: Artificial Sequence
<220> FEATURE:
<223> OTHER INFORMATION: Primer aspC-F

<400> SEQUENCE: 57
ggctctagaa cacaggaaac agaccatgtt tgagaacatt accgcc        46

<210> SEQ ID NO 58
<211> LENGTH: 47
<212> TYPE: DNA
<213> ORGANISM: Artificial Sequence
<220> FEATURE:
<223> OTHER INFORMATION: Primer aspC-R

<400> SEQUENCE: 58
ggcgcatgcg acctcgaggt agtcgactta cagcactgcc acaatcg        47

<210> SEQ ID NO 59
<211> LENGTH: 42
<212> TYPE: DNA
<213> ORGANISM: Artificial Sequence
<220> FEATURE:
<223> OTHER INFORMATION: Primer lysC-rbs2-F

<400> SEQUENCE: 59
atttcacaca ggaaacagct atgtctgaaa ttgttgtctc ca        42

<210> SEQ ID NO 60
<211> LENGTH: 20
<212> TYPE: DNA
<213> ORGANISM: Artificial Sequence
<220> FEATURE:
<223> OTHER INFORMATION: Primer lysC-rbs2-R

<400> SEQUENCE: 60
agctgtttcc tgtgtgaaat        20

<210> SEQ ID NO 61
<211> LENGTH: 46

```
<212> TYPE: DNA
<213> ORGANISM: Artificial Sequence
<220> FEATURE:
<223> OTHER INFORMATION: Primer asd-rbs2-F

<400> SEQUENCE: 61
atttcacaca ggaaacagct atgaaaaatg ttggttttat cggctg        46

<210> SEQ ID NO 62
<211> LENGTH: 20
<212> TYPE: DNA
<213> ORGANISM: Artificial Sequence
<220> FEATURE:
<223> OTHER INFORMATION: Primer asd-rbs2-R

<400> SEQUENCE: 62
agctgtttcc tgtgtgaaat        20

<210> SEQ ID NO 63
<211> LENGTH: 29
<212> TYPE: DNA
<213> ORGANISM: Artificial Sequence
<220> FEATURE:
<223> OTHER INFORMATION: Primer SacI-F2

<400> SEQUENCE: 63
ggcgagctct cccctgattc tgtggataa        29

<210> SEQ ID NO 64
<211> LENGTH: 29
<212> TYPE: DNA
<213> ORGANISM: Artificial Sequence
<220> FEATURE:
<223> OTHER INFORMATION: Primer SacI-R2

<400> SEQUENCE: 64
ggcgagctca gcaaaaggcc aggaaccgt        29

<210> SEQ ID NO 65
<211> LENGTH: 30
<212> TYPE: DNA
<213> ORGANISM: Artificial Sequence
<220> FEATURE:
<223> OTHER INFORMATION: Primer ApaI-F

<400> SEQUENCE: 65
ggcgggcccg tattaccgcc tttgagtgag        30

<210> SEQ ID NO 66
<211> LENGTH: 29
<212> TYPE: DNA
<213> ORGANISM: Artificial Sequence
<220> FEATURE:
<223> OTHER INFORMATION: Primer ApaI-R

<400> SEQUENCE: 66
ggcgggccca cagaatcagg ggagagctc        29

<210> SEQ ID NO 67
<211> LENGTH: 29
<212> TYPE: DNA
<213> ORGANISM: Artificial Sequence
<220> FEATURE:
<223> OTHER INFORMATION: Primer LAL2-SacI-F

<400> SEQUENCE: 67
```
ggcgagctcg ttggccgatt cattaatgc                                       29

<210> SEQ ID NO 68
<211> LENGTH: 30
<212> TYPE: DNA
<213> ORGANISM: Artificial Sequence
<220> FEATURE:
<223> OTHER INFORMATION: Primer LAL2-ApaI-R

<400> SEQUENCE: 68
ggcgggccct taaagcaatt ccagcgccag                                      30

<210> SEQ ID NO 69
<211> LENGTH: 30
<212> TYPE: DNA
<213> ORGANISM: Artificial Sequence
<220> FEATURE:
<223> OTHER INFORMATION: Primer csrB-F

<400> SEQUENCE: 69
ggcgagctcg agtcagacaa cgaagtgaac                                      30

<210> SEQ ID NO 70
<211> LENGTH: 34
<212> TYPE: DNA
<213> ORGANISM: Artificial Sequence
<220> FEATURE:
<223> OTHER INFORMATION: Primer csrB-R

<400> SEQUENCE: 70
ggcggatcca ataaaaaaag ggagcactgt attc                                 34

<210> SEQ ID NO 71
<211> LENGTH: 30
<212> TYPE: DNA
<213> ORGANISM: Artificial Sequence
<220> FEATURE:
<223> OTHER INFORMATION: Primer csrC-F

<400> SEQUENCE: 71
ggcgagctca tagagcgagg acgctaacag                                      30

<210> SEQ ID NO 72
<211> LENGTH: 33
<212> TYPE: DNA
<213> ORGANISM: Artificial Sequence
<220> FEATURE:
<223> OTHER INFORMATION: Primer csrC-R

<400> SEQUENCE: 72
ggcggatcca agaaaaaagg cgacagatta ctc                                  33

<210> SEQ ID NO 73
<211> LENGTH: 30
<212> TYPE: DNA
<213> ORGANISM: Artificial Sequence
<220> FEATURE:
<223> OTHER INFORMATION: Primer csrB-F2

<400> SEQUENCE: 73
ggcggatccc acacaggagg agctcgagtc                                      30

<210> SEQ ID NO 74
<211> LENGTH: 34
<212> TYPE: DNA
<213> ORGANISM: Artificial Sequence

```
<220> FEATURE:
<223> OTHER INFORMATION: Primer csrB-R2

<400> SEQUENCE: 74
ggcgcatgca ataaaaaaag ggagcactgt attc                                34

<210> SEQ ID NO 75
<211> LENGTH: 31
<212> TYPE: DNA
<213> ORGANISM: Artificial Sequence
<220> FEATURE:
<223> OTHER INFORMATION: Primer csrC-F2

<400> SEQUENCE: 75
ggcggatccc acacaggagg agctcataga g                                   31

<210> SEQ ID NO 76
<211> LENGTH: 33
<212> TYPE: DNA
<213> ORGANISM: Artificial Sequence
<220> FEATURE:
<223> OTHER INFORMATION: Primer csrC-R2

<400> SEQUENCE: 76
ggcgcatgca agaaaaaagg cgacagatta ctc                                 33
```